(12) United States Patent
Hubbard et al.

(10) Patent No.: US 7,060,287 B1
(45) Date of Patent: Jun. 13, 2006

(54) TISSUE AUGMENTATION MATERIAL AND METHOD

(75) Inventors: William G. Hubbard, Burlington, WI (US); Timothy R. Devine, Whitefish Bay, WI (US)

(73) Assignee: Bioform Inc., San Mateo, CA (US)

( * ) Notice: Subject to any disclaimer, the term of this patent is extended or adjusted under 35 U.S.C. 154(b) by 0 days.

(21) Appl. No.: 09/626,326

(22) Filed: Jul. 26, 2000

Related U.S. Application Data

(63) Continuation-in-part of application No. 09/288,999, filed on Aug. 4, 1998, now Pat. No. 6,432,437, which is a continuation of application No. 08/538,444, filed on Oct. 3, 1995, now Pat. No. 5,922,025, which is a division of application No. 08/159,071, filed on Nov. 29, 1993, which is a continuation of application No. 07/999,411, filed on Jan. 21, 1993, now abandoned, which is a continuation-in-part of application No. 07/833,874, filed on Feb. 11, 1992, now abandoned

(60) Provisional application No. 60/148,590, filed on Aug. 13, 1999.

(51) Int. Cl.
*A61F 2/00* (2006.01)
*A61F 2/02* (2006.01)

(52) U.S. Cl. .................. 424/423; 424/426; 523/114; 523/115; 623/11.11

(58) Field of Classification Search ............ 623/11.11; 424/423, 426; 523/114, 115
See application file for complete search history.

(56) References Cited

U.S. PATENT DOCUMENTS

| | | | |
|---|---|---|---|
| 3,527,217 A | 9/1970 | Gettig | 128/221 |
| 3,703,575 A | 11/1972 | Thiele | 3/1 |
| 4,107,288 A | 8/1978 | Oppenheim et al. | 424/22 |
| 4,123,091 A | 10/1978 | Cosentino et al. | 285/39 |

(Continued)

FOREIGN PATENT DOCUMENTS

| | | |
|---|---|---|
| CA | 2029338 | 5/1991 |
| CH | 643732 | 1/1978 |
| EP | 0196143 | 10/1986 |
| GB | 2 227 176 A | 7/1990 |
| JP | 61101447 | 5/1986 |
| JP | 6211459 | 1/1987 |
| NL | 8304129 | 7/1985 |
| WO | 87/04110 | 7/1987 |
| WO | WO91/17777 | 11/1991 |
| WO | WO99/02107 | 1/1999 |

OTHER PUBLICATIONS

"Artificial Urinary Sphincter & Periurethral Injections," Appell, Rodney A., M.D.; Obstetrics and Gynecology Report, vol. 2, No. 3, pp. 334–342, 1990.

(Continued)

*Primary Examiner*—Carlos A. Azpuru
(74) *Attorney, Agent, or Firm*—Foley & Lardner LLP

(57) ABSTRACT

A permanent, biocompatible material for soft tissue augmentation. The biocompatible material comprises a matrix of smooth, round, finely divided, substantially spherical particles of a biocompatible ceramic material, close to or in contact with each other, which provide a scaffold or lattice for autogenous, three dimensional, randomly oriented, non-scar soft tissue growth at the augmentation site. The augmentation material can be homogeneously suspended in a biocompatible, resorbable lubricious gel carrier comprising a polysaccharide. This serves to improve the delivery of the augmentation material by injection to the tissue site where augmentation is desired. The augmentation material is especially suitable for urethral sphincter augmentation, for treatment of incontinence, for filling soft tissue voids, for creating soft tissue blebs, for the treatment of unilateral vocal cord paralysis, and for mammary implants. It can be injected intradermally, subcutaneously or can be implanted.

73 Claims, 3 Drawing Sheets

U.S. PATENT DOCUMENTS

| | | | |
|---|---|---|---|
| 4,191,747 A | 3/1980 | Scheicher | 424/94 |
| 4,197,846 A | 4/1980 | Bucalo | 128/218 P |
| 4,322,398 A | 3/1982 | Reiner et al. | 424/19 |
| 4,330,614 A | 5/1982 | Mayer et al. | 430/325 |
| 4,373,217 A | 2/1983 | Draenert | 3/19 |
| 4,440,754 A | 4/1984 | Sorenson | 424/140 |
| 4,619,655 A | 10/1986 | Hanker et al. | 623/1 |
| 4,657,548 A | 4/1987 | Nichols | 623/10 |
| 4,693,986 A | 9/1987 | Vit et al. | 501/1 |
| 4,776,890 A | 10/1988 | Chu | 106/161 |
| 4,795,467 A | 1/1989 | Piez et al. | 623/16 |
| 4,803,075 A | 2/1989 | Wallace et al. | 424/423 |
| 4,842,603 A | 6/1989 | Draenert | 623/16 |
| 4,849,285 A | 7/1989 | Dillon | 428/330 |
| 5,007,940 A | 4/1991 | Berg | 623/66 |
| 5,011,495 A | 4/1991 | Hollinger | 623/16 |
| 5,034,352 A | 7/1991 | Vit et al. | 501/1 |
| 5,035,711 A | 7/1991 | Aoki et al. | 623/11 |
| 5,067,965 A | 11/1991 | Ersek et al. | 623/66 |
| 5,075,360 A | 12/1991 | Fitt et al. | 524/48 |
| 5,116,387 A | 5/1992 | Berg | 623/66 |
| 5,126,141 A | 6/1992 | Henry | 424/423 |
| 5,140,016 A | 8/1992 | Goldberg et al. | 514/57 |
| 5,141,561 A | 8/1992 | Ledard et al. | 106/35 |
| 5,143,724 A | 9/1992 | Leshchiner et al. | 424/78.08 |
| 5,158,573 A | 10/1992 | Berg | 623/66 |
| 5,192,802 A | 3/1993 | Rencher | 514/535 |
| 5,204,382 A | 4/1993 | Wallace et al. | 523/115 |
| 5,246,698 A | 9/1993 | Leshchiner et al. | 424/78.08 |
| 5,258,028 A | 11/1993 | Ersek et al. | 623/11 |
| 5,266,248 A | 11/1993 | Ohtsuka et al. | 264/44 |
| 5,306,302 A | 4/1994 | Bauer et al. | 623/16 |
| 5,324,775 A * | 6/1994 | Rhee et al. | 525/54.2 |
| 5,336,263 A | 8/1994 | Ersek et al. | 623/11 |
| 5,344,452 A | 9/1994 | Lemperle | 623/11 |
| 5,352,715 A | 10/1994 | Wallace et al. | 523/115 |
| 5,399,351 A | 3/1995 | Leshchiner et al. | 424/422 |
| 5,451,406 A | 9/1995 | Lawin et al. | 424/423 |
| 5,480,644 A | 1/1996 | Freed | 424/436 |
| 5,490,984 A | 2/1996 | Freed | 424/436 |
| 5,523,291 A | 6/1996 | Janzen et al. | 514/21 |
| 5,571,182 A | 11/1996 | Ersek et al. | 623/11 |
| 5,573,771 A | 11/1996 | Geistlich et al. | 424/422 |
| 5,591,453 A | 1/1997 | Ducheyne et al. | 424/484 |
| 5,626,861 A | 5/1997 | Laurencin et al. | 424/426 |
| 5,637,101 A | 6/1997 | Shillington | 604/242 |
| 5,702,677 A | 12/1997 | Shimp et al. | 423/308 |
| 5,709,875 A | 1/1998 | Lebugle et al. | 424/426 |
| 5,752,974 A | 5/1998 | Rhee et al. | 606/214 |
| 5,766,618 A | 6/1998 | Laurencin et al. | 424/426 |
| 5,792,478 A | 8/1998 | Lawin et al. | 424/502 |
| 5,827,937 A | 10/1998 | Agerup | 536/123.12 |
| 5,837,752 A | 11/1998 | Shastri et al. | 523/116 |
| 5,853,398 A | 12/1998 | Lal et al. | 604/250 |
| 5,854,382 A | 12/1998 | Loomis | 528/354 |
| 5,861,176 A | 1/1999 | Ducheyne et al. | 424/486 |
| 6,165,514 A | 12/2000 | Bockman et al. | 424/495 |

OTHER PUBLICATIONS

"Periurethral Teflon Injection for Urinary Incontinence," Politano et al., Journal of Urology, pp. 180–183, vol. III, Feb., 1974.

"PMMA Microspheres for Intradermal Implanation: Part 1. Animal Research," Lemperle et al.; Animal Research Ann. Plas. Surg., 1991; 26:57–63.

"Migration & Granulomatous Reaction After Periurethral Injection of Polytef (Teflon)," Malizia et al. JAMA, Jun. 22/29, 1984—vol. 251, No. 24.

"Pulmonary Migration Following Periurethral Polytetrafluoroethylene Injection for Urinary Incontinence," Claes et al., Journal of Urology 142:821–822, 1989.

"Histologic Observation of Soft Tissue Responses to Implanted, Multifaceted Particles and Discs of Hydroxylapatite," Drobeck et al., J. of Oral Maxillofac. Surg., 42:143–149, 1984.

"Soft Tissue Responses to Hydroxylapatite Particles of Different Shapes," Misiek et al.; J. of Oral Maxillofac. Surg.; 42:150–160, 1984.

"Subcutaneous Tissue Responses in Rats to Injection of Fine Particles of Synthetic Hydroxyapatite Ceramic," Shimizu, Shin–ichi; Biomedical Research, 9 (2) 95–111, 1988.

"Bioplastique: A New Textured Copolymer Microparticle Promises Permanence in Soft Tissue Augmentation," Ersek et al.; Plastic and Reconstructive Surgery, Apr. 1991, pp. 693–701.

"Bioglass®—A Suspension for Treatment of Urinary Incontinence," Ramer et al., 16th Annual Meeting of the Society for Biomaterials, May 20–23, 1990.

"Hylan Gel for Soft Tissue Augmentation," Larsen et al., 16th Annual Meeting of the Society for Biomaterials, May 20–23, 1990.

Lehtenen et al., "Soft Tissue Response to Hydroxyapatite Particles of Different Shapes in Rabbit Tibia," *J. Oral Maxillofac. Surg.*, 1990, pp. 48:1075–1078.

"Remington's Pharmaceutical Sciences," Gennaro, Ed., 18th Edition, 1990, pp. 1304–1305 and 1316.

Van Vlack et al., "Elements of Materials Science," *Addison Wesley* (1964) pp. 379–380.

Dental Implants, in Bioceramics of Calcium Phosphate, Klaas deGroot, (ed), CRC Press, pp. 115–129 (1983).

Hench, "Ceramics in Substitutive and Reconstructive Surgery," *Elsevier Science Publishers B.V.* (1991) pp. 259–274.

Caro et al., "The Mechanics of the Circulation," *Oxford University Press* (1978) p. 156.

* cited by examiner

TISSUE AUGMENTATION MATERIAL AND METHOD

This is a continuation-in-part of application Ser. No. 09/288,999 filed Aug. 4, 1998, U.S. Pat. No. 6,432,437, which is a continuation of application Ser. No. 08/538,444 filed on Oct. 3, 1995 and issued on Jul. 13, 1999 as U.S. Pat. No. 5,922,025, which is a division of application Ser. No. 08/159,071 filed Nov. 29, 1993, which is a file wrapper continuation of application Ser. No. 07/999,411 filed Jan. 21, 1993, abandoned, which is a continuation-in-part of application Ser. No. 07/833,874, filed Feb. 11, 1992, abandoned.

This application claims priority to Provisional Application No. 60/148,590 filed Aug. 13, 1999.

FIELD OF THE INVENTION

This invention relates to biocompatible compositions for soft tissue augmentation more specifically urethral sphincter augmentation for treatment of incontinence, for filling soft tissue voids or creating soft tissue blebs, for mammary implants, and for the treatment of unilateral vocal cord paralysis.

This invention also relates to a gel carrier for the biocompatible compositions.

BACKGROUND OF THE INVENTION

Examples of biocompatible materials that have been proposed for use in augmenting soft tissue in the practice of plastic and reconstructive surgery, include collagen, gelatin beads, beads of natural or synthetic polymers, such as polytetrafluoroethylene, silicone rubber and various hydrogel polymers, such as polyacrylonitrile-polyacrylamide hydrogels.

Most often, the biomaterials are delivered to the tissue site where augmentation is desired by means of an injectable composition which comprises the biomaterial and a biocompatible fluid that acts as a lubricant to improve the injectability of the biomaterial suspension. The injectable biomaterial compositions can be introduced into the tissue site by injection from a syringe intradermally or subcutaneously into humans or other mammals to augment soft tissue, to correct congenital anomalies, acquired defects or cosmetic defects. They may also be injected into internal tissues such as tissue defining sphincters to augment such tissue in the treatment of incontinence, and for the treatment of unilateral vocal cord paralysis.

U.K Patent Application No. 2,227,176 to Ersek et al, relates to a microimplantation method for filling depressed scars, unsymmetrical orbital floors and superficial bone defects in reconstructive surgery procedures using microparticles of about 20 to 3,000 microns which may be injected with an appropriate physiologic vehicle and hypodermic needle and syringe in a predetermined locus such as the base of depressed scars, beneath skin areas of depression and beneath perichondrium or periosteum in surface irregularities of bone and cartilage. Textured microparticles can be used, including silicone, polytetrafluoroethylene, ceramics or other inert substances. In those instances wherein the requirement is for hard substances, biocompatible material such as calcium salts including hydroxyapatite or crystalline materials, biocompatible ceramics, biocompatible metals such as stainless steel particles or glass may be utilized. Appropriate physiological vehicles have been suggested, including saline, various starches, polysaccharides, and organic oils or fluids.

U.S. Pat. No. 4,803,075 to Wallace et al, relates to an injectable implant composition for soft tissue augmentation comprising an aqueous suspension of a particulate biocompatible natural or synthetic polymer and a lubricant to improve the injectability of the biomaterial suspension.

U.S. Pat. No. 4,837,285 to Berg et al, relates to a collagen-based composition for augmenting soft tissue repair, wherein the collagen is in the form of resorbable matrix beads having an average pore size of about 50 to 350 microns, with the collagen comprising up to about 10% by volume of the beads.

U.S. Pat. No. 4,280,954 to Yannas et al, relates to a collagen-based composition for surgical use formed by contacting collagen with a mucopolysaccharide under conditions at which they form a reaction product and subsequently covalently crosslinking the reaction product.

U.S. Pat. No. 4,352,883 to Lim discloses a method for encapsulating a core material, in the form of living tissue or individual cells, by forming a capsule of polysaccharide gums which can be gelled to form a shape retaining mass by being exposed to a change in conditions such as a pH change or by being exposed to multivalent cations such as calcium.

Namiki, "Application of Teflon Paste for Urinary Incontinence-Report of Two Cases," *Urol. Int.*, Vol. 39, pp. 280–282, (1984), discloses the use of a polytetrafluoroethylene paste injection in the subdermal area to treat urinary incontinence.

Drobeck et al, "Histologic Observation of Soft Tissue Responses to Implanted, Multifaceted Particles and Discs of Hydroxylapatite,." *Journal of Oral Maxillofacial Surgery*, Vol. 42, pp. 143–149, (1984), discloses that the effects on soft tissue of long and short term implants of ceramic hydroxylapatite implanted subcutaneously in rats and subcutaneously and subperiosteally in dogs. The inventions consisted of implanting hydroxylapatite in various sizes and shapes for time periods ranging from seven days to six years to determine whether migration and/or inflammation occurred.

Misiek et al., "Soft Tissue Responses to Hydroxylapatite Particles of Different Shapes," *Journal of Oral Maxillofacial Surcery*, Vol. 42, pp. 150–160, (1984), discloses that the implantation of hydroxylapatite in the form of sharp edged particles or rounded particles in the buccal soft tissue pouches produced inflammatory response at the implant sites with both particle shapes. Each of the particles weighed 0.5 grams. However, inflammation resolved at a faster rate at the sites implanted with the rounded hydroxylapatite particles.

Shimizu, "Subcutaneous Tissue Responses in Rats to Injection of Fine Particles of Synthetic Hydroxyapatite Ceramic," *Biomedical Research*, Vol. 9, No. 2, pp. 95–111 (1988), discloses that subcutaneous injections of fine particles of hydroxyapatite ranging in diameter from about 0.65 to a few microns and scattered in the tissue were phagocytized by macrophages in extremely early stages. In contrast, larger particles measuring several microns in diameter were not phagocytized, but were surrounded by numerous macrophages and multinucleated giant cells. It was also observed that the small tissue responses to hydroxyapatite particles were essentially a non-specific foreign body reaction without any cell or tissue damage.

R. A. Appell, "The Artificial Urinary Sphincter and Periurethral Injections," *Obstetrics and Gynecolocy Report* Vol. 2, No. 3, pp. 334–342, (1990), is a survey article disclosing various means of treating urethral sphincteric incompetence, including the use of injectables such as polytetrafluoroethylene micropolymer particles of about 4 to 100 microns in size in irregular shapes, with glycerin and polysorbate.

Another periurethral injectable means consists of highly purified bovine dermal collagen that is crosslinked with glutaraldehyde and dispersed in phosphate-buffered physiologic saline.

Politano et al, "Periurethral Teflon Injection for Urinary Incontinence," *The Journal of Urology*, Vol. 111, pp. 180–183 (1974), discloses the use of Polytetrafluoroethylene paste injected into the urethra and the periurethral tissues to add bulk to these tissues to restore urinary control in both female and male patients having urinary incontinence.

Malizia et al, "Migration and Granulomatous Reaction After Periurethral Injection of Polytef (Teflon)," *Journal of the American Medical Association*, Vol. 251, No. 24, pp. 3277–3281, June 22–29 (1984), discloses that although patients with urinary incontinence have been treated successfully by periurethral injection of polytetrafluoroethylene paste, a study in continent animals demonstrates migration of the polytetrafluoroethylene particles from the inspection site.

Claes et al, "Pulmonary Migration Following Periurethral Polytetrafluoroethylene Injection for Urinary Incontinence," *The Journal of Urology*, Vol. 142, pp. 821–2, (September 1989), confirms the finding of Malizia in reporting a case of clinically significant migration of polytetrafluoroethylene paste particles to the lungs after periurethral injection.

Ersek et al, "Bioplastique: A New Textured Copolymer Microparticle Promises Permanence in Soft-Tissue Augmentation," *Plastic and Reconstructive Surgery*, Vol. 87, No. 4, pp. 693–702, (April 1991), discloses the use of a biphasic copolymer made of fully polymerized and vulcanized methylmethylpolysiloxane mixed with a plasdone hydrogel, and used in reconstructing cleft lips, depressed scars of chicken pox and indentations resulting from liposuction, glabella frown wrinkles and soft tissue augmentation of thin lips. The biphasic copolymer particles were found to neither migrate nor become absorbed by the body were textured and had particle sizes varying from 100 to 600 microns.

Lemperle et al. "PMMA Microspheres for Intradermal Implantation: Part I. Animal Research," *Annals of Plastic Surgery*, Vol. 26, No. 1, pp. 57–63, (1991), discloses the use of polymethylmethacrylate microspheres having particle sizes of 10 to 63 microns in diameter used for correction of small deficiencies within the dermal corium to treat wrinkles and acne scars.

Kresa et al, "Hydron Gel Implants in Vocal Cords," *Otolaryngolocy Head and Neck Surgery*, Vol. 98. No. 3, pp. 242–245, (March 1988), discloses a method for treating vocal cord adjustment where there is insufficient closure of the glottis which comprises introducing a shaped implant of a hydrophilic gel that has been previously dried to a glassy, hard state, into the vocal cord.

Hirano et al, "Transcutaneous Intrafold Injection for Unilateral Vocal Cord Paralysis: Functional Results," *Ann. Otol. Rhinol. Laryncol.*, Vol. 99, pp. 598–604 (1990), discloses the technique of transcutaneous intrafold silicone injection in treating glottic incompetence caused by unilateral vocal fold paralysis. The silicone injection is given under a local anesthetic with the patient in a supine position, wherein the needle is inserted through the cricothyroid space.

Hill et al, "Autologous Fat Injection for Vocal Cord Medialization in the Canine Larynx," *Laryngoscope*, Vol. 101, pp. 344–348 (April 1991), discloses the use of autologous fat as an alternative to Teflon® collagen as the implantable material in vocal cord medialization, with a view to its use as an alternative to non-autologous injectable material in vocal cord augmentation.

Mikaelian et al, "Lipoinjection for Unilateral Vocal Cord Paralysis," *Laryngoscope*, Vol. 101, pp. 4654–68 (May 1991), discloses that the commonly used procedure of injecting Teflon® paste to improve the caliber of voice in unilateral vocal cord paralysis has a number of drawbacks, including respiratory obstruction from overinjected Teflon® and unsatisfactory voice quality. In this procedure, lipoinjection of fat commonly obtained from the abdominal wall appears to.impart a soft bulkiness to the injected cord while allowing it to retain its vibratory qualities. The injected fat is an autologous material which can be retrieved if excessively overinjected.

Strasnick et al, "Transcutaneous Teflon® Injection for Unilateral Vocal Cord Paralysis: An Update," *Laryngoscope*, Vol. 101, pp. 785–787 (July 1991), discloses the procedure of Teflon® injection to restore glottic competence in cases of paralytic dysphonia.

SUMMARY OF THE INVENTION

In accordance with the present invention, there is provided a permanent, biocompatible material for soft tissue augmentation, and methods for its use. There is also provided in accordance with the present invention a gel carrier which is particularly advantageous for the administration of the biocompatible material to the desired tissue augmentation site.

The biocompatible material comprises a matrix of smooth, rounded, substantially spherical, finely divided particles of a biocompatible ceramic material, close to or in contact with each other, which provide a scaffold or lattice for autogenous, three dimensional, randomly oriented, non-scar soft tissue growth at the augmentation site. The augmentation material can be homogeneously suspended, for example, in a biocompatible, resorbable lubricious gel carrier comprising, e.g., a polysaccharide. This serves to improve the delivery of the augmentation material by injection to the tissue site where augmentation is desired. The augmentation material is especially suitable for urethral sphincter augmentation, for treatment of incontinence, for filling soft tissue voids, for creating soft tissue blebs, for the treatment of unilateral vocal cord paralysis, and for mammary implants. It can be injected intradermally or subcutaneously or can be implanted.

DESCRIPTION OF THE DRAWINGS

In the accompanying drawings.

DESCRIPTION OF THE PREFERRED EMBODIMENTS

In instances of urinary incontinence, such as stress incontinence in women, or after a prostatectomy in men, it is necessary to compress the urethra to assist the sphincter muscle in closing to avoid leakage of urine from the bladder.

The soft tissue augmentation material of the present invention comprises an injection system which can be used to add bulk and localize compression to the sphincter muscle/urethra, thereby reducing the lumen size through one or more injections of the augmentation material and thus substantially reduce or eliminate urinary stress incontinence due to incompetent sphincters in females and males.

The augmentation material can also be used in filling and smoothing out soft tissue defects such as pock marks or scars. Further use for the augmentation material can be for intracordal injections of the laryngeal voice generator by changing the shape of this soft tissue mass. The procedure involves delivering the augmentation material to the site of treatment, preferably by injection. The augmentation material or gel can also be used for mammary implants.

Figure 1:
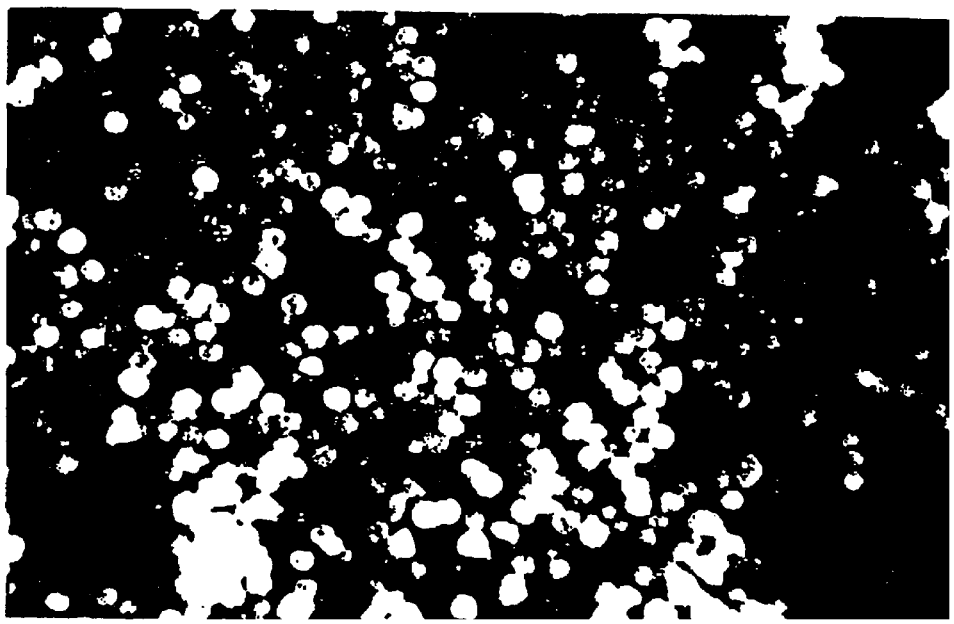
FIG. 1 is a photomicrograph of smooth, round calcium hydroxyapatite particles at 40× magnification.

The inventive augmentation material comprises smooth rounded, substantially spherical, particles of a ceramic material. The term "substantially spherical" refers to the fact that while some of the present particles may be spheres, most of the particles of the present invention are sphere-like in their shape, i.e., they are spheroidal. FIG. 1 is illustrative of these spheroidal or substantially spherical characteristics. The terms "rounded" or "smooth, rounded" as used herein refers to the fact even though the present particles are not perfect spheres, they do not have any sharp or angular edges. The particles must be sufficiently large so as to avoid phagocytosis, as is further discussed below. As an upper limit the particles can be any size suitable for the desired soft tissue augmentation. However, it is understood that for introduction by injection the upper limit on particle size will be dictated by the particular injection equipment employed. That is, the particles must be sufficiently small so as to avoid aggregation and clogging of the syringe when being injected. A typical range for injection is from about 35 to 150 microns, preferably in a narrow particle size range extending not more than about 35 microns, and more preferably extending not more than about 10 to 30 microns, and most preferably having substantially equivalent particle sizes. For example, the ceramic material can have a uniform particle size distribution of about 35 to 65 microns, or 75 to 100 microns or 100 to 125 microns. These are meant to be exemplary and not limiting. Other narrow particle size ranges within the overall size range of 35 to 150 microns can also be used. In discussing these ranges, it should be understood that as a practical matter, a small amount of particles outside the desired range may be present in a sample of the present augmentation material. However, most of the particles in any given sample should be within the desired range. Preferably, 90% of the particles are within the desired range and most preferably 95–99% are within the range.

The finely divided ceramic augmentation material is substantially non-resorbable so that repetitious corrections are not necessary. By "substantially non-resorbable" is meant that although some dissolution of the augmentation material may take place over time, it is sufficiently slow so as to allow for replacement with growing tissue cells. There is no antigenic response because there are no amino acids as in collagen and fibrinogen. The ceramic material is highly biocompatible and can be injected through an 18 gauge or smaller opening syringe.

The preferred ceramic material is calcium hydroxyapatite, also known as basic calcium orthophosphate, or calcium hydroxylapatite, and is the natural mineral phase of teeth and bones. As an implant material, granular calcium hydroxyapatite, which is a sintered polycrystalline composite of calcium phosphate, has proven to be highly compatible in tissue.

One method for preparing dense, rounded or substantially spherical ceramic particles such as calcium hydroxyapatite is by spray drying a slurry of about 20 to 40 weight % submicron particle size calcium hydroxyapatite. This material is commercially available or can be prepared by means known in the art such as by low temperature crystallization methods, hydrothermal crystallization methods, solid-solid reaction and the like. The slurry can also include processing additives such as wetting agents and binders, on the order of about 1 to 5 weight %. Suitable wetting agents include polysorbate, sodium oxalate, ammonium polyelectrolyte. Suitable binders include polyvinyl alcohol, dextrin or carbowax.

The slurry is spray dried by pumping it through a nozzle to form globules that are forced through a column of heated air to remove the moisture. The agglomerated particles dry in substantially spherical shape and are collected at one end of the heated column.

The substantially spherical particles are then sintered in a crucible at temperatures of about 1050 to 1200° C. for at least one hour. To minimize further agglomeration, a presintering operation at about 800 to 1000° C. for about one hour can be employed.

After the presintering operation, the globular particles can be agitated or rolled to prevent the individual particles from sticking or clumping together. A rotary calcining furnace can be used for this purpose. This type of furnace rotates so that the agglomerated particles roll over one another during the sintering process thereby minimizing the clumping together of the particles. A commercial source of such spray dried particles is CeraMed Corp., Lakewood, Colo.

An alternative method for forming dense, spherical particles is by rotary agglomeration, wherein the fine, submicron ceramic particles, such as calcium hydroxyapatite, are placed on a large diameter rotating bowl that is at least about 3 feet in diameter.

The bowl is rotated on its axis at an angle of approximately thirty degrees, with its speed and angle of rotation adjusted so that the submicron particles roll across the face of the bowl. A fine. spray of binder solution, such as those described above, is then sprayed on the particles at a rate which just wets the particles. The rolling action across the face of the bowl and the addition of the binder solution causes the particles to form small rolling agglomerates that grow in size as the operation continues. The operation is comparable to forming a large ball of snow by rolling a small snowball down a hill. The operating conditions, such as the size of bowl, speed of rotation, angle of rotation and amount of spray used which define the size and density of the agglomerates formed, are well known to those skilled in the art. The agglomerated spherical particles can then be sintered in a manner similar to the spray dried agglomerates.

The resulting sintered spherical particles can then be separated and classified by size by means of well known sieving operations through specifically sized mesh screens. The particle size distribution and density can also be evaluated to ensure suitability for a particular application. A commercial source of such rotary agglomerated particles is CAM Implants, Leiden, The Netherlands.

Further surface refining or smoothing can be accomplished by a milling operation, such as ball milling. Extra mini-grinding media can be used, but to minimize contamination, the spherical particles can be milled on themselves. This can be done in a standard jar mill or an inclined rotation mill by adding sufficient amounts of purified water to the particles to ensure that the particles roll evenly over each other. This can be done for long periods such as several days to make the surface smooth on the round agglomerates. If the starting agglomerates are not round, they can be made smooth but not round by rolling. Irregularly shaped agglomerates, although having a smooth surface, can jam, obstruct or significantly increase the injection force on a syringe needle when injected into tissue.

The agglomerated spherical particles can also be washed free of small particles by using an inclined rotation mill. This can be done by placing the agglomerates in the mill with purified water and rolled for a sufficient time, such as one hour. The supernate is then poured off and more purified water is added. The process is repeated until the supernate is relatively clear after a rotating cycle, and usually takes about three or four operations.

The methods described above are suitable for any ceramic materials which may be employed.

A smooth surface on the individual round, spherical particles is important to reduce and minimize surface porosity. Surface smoothness can be improved by finishing operations known in the art, such as surface milling and the like. It is preferred that such smoothing operations be capable of minimizing surface irregularities on the individual particles so that the surface appears similar to that of a smooth round bead when viewed under a microscope at 40× magnification. This is apparent from FIG. 1, which is a photomicrograph of calcium hydroxyapatite particles having a particle size distribution of 38 to 63 microns. The smooth, round substantially spherical and non-porous surface is readily evident.

The ceramic particles are preferably smooth, hard, rounded particles, having a density on the order of about 75 to 100%, and preferably about 95 to 100% of the theoretical density of desired ceramic material, e.g., calcium hydroxyapatite. The finishing operations can also minimize the surface porosity of the calcium hydroxyapatite particles to less than about 30%, and preferably less than about 10%. This is preferred, because by minimizing surface porosity, particles with smooth surfaces can be obtained, thereby eliminating -jagged, irregular surfaces and maximizing the ability of the smooth, round particles to flow easily in contact with each other.

Although this invention is described in terms of calcium hydroxyapatite, other suitable materials useful herein include, but are not limited to, calcium phosphate-based materials, alumina-based materials and the like. Examples include, but are not limited to, tetracalcium phosphate, calcium pyrophosphate, tricalcium phosphate, octacalcium phosphate, calcium fluorapatite, calcium carbonate apatite, and combinations thereof. Other equivalent calcium based compositions can also be used such as calcium carbonate, and the like.

As noted, the individual ceramic particles used in the present invention have a generally smooth, round, preferably spherical shape, in contrast to particles with more textured porous surfaces or openings, and having jagged, irregular shapes or shapes with straight edges. The smooth round shape enables the ceramic particles to be more easily extruded and to flow with reduced friction from a syringe into the tissue site where soft tissue augmentation is desired. Once at the tissue site, the ceramic particles provide a matrix or scaffolding for autogenous tissue growth.

As mentioned above, particle sizes in the range of about 35 to 150 microns are optimal to minimize the possibility of particle migration by phagocytosis and to facilitate injectability. Phagocytosis occurs where smaller particles on the order of 15 microns or less become engulfed by the cells and removed by the lymphatic system from the site where the augmentation material has been introduced into the tissues, generally by injection.

At the lower end, particles greater than 15 microns and typically 35 microns or above are too large to be phagocytosized, and can be easily separated by known sizing techniques. Thus, it is relatively simple to produce the narrow or equivalent particle size ranges that are most desirable for use in this invention.

It is also desirable to use a narrow or equivalent particle size range of ceramic particles due to the fact that a distribution of such smooth, round, substantially spherical particles reduces friction, and facilitates the ease of injecting the particles by needle from a syringe into the skin tissue at the desired augmentation site. This is in contrast to the use of the more porous, textured, irregularly shaped particles which tend to increase the frictional forces, and are much more difficult to deliver by injection.

As discussed above, the particle size distribution, or range of particle sizes of the ceramic material within the overall range of 35 to 150 microns is preferably minimized to a more narrow or equivalent particle size range. This maximizes the intraparticle void volume, or interstitial volume, into which autogenous tissue growth, stimulated by the presence of the augmentation material, can occur. A greater interstitial volume exists between particles that are equivalent in size, compared with particles having a variable size distribution. In the context of this invention, the interstitial volume is the void space existing between particles of the augmentation material that are close to or in contact with each other.

For example, in crystalline lattice structures such as face centered cubic, body centered cubic and simple cubic, the percentage of interstitial void space, known as the atomic packing factor, is 26%, 33%, and 48%, respectively. This is independent of the diameter of the atom or in this case, the particle. Since the ceramic particles never pack as tightly as the atoms in a crystalline lattice structure, the void volume would be even greater, thereby maximizing the growth of autogenous tissue.

To extend the analogy of the crystalline structure a step further, the interstitial opening defines the maximum size that a particle can fit into a normally occurring void space in the structure. The largest interstitial space is about 0.4 times the size of the mean ceramic particle in the particle size distribution.

Thus, if the particle size distribution is about 35 to 65 microns, the mean particle size would be 50 microns. The largest interstitial space would be 50×0.4=20 microns. Since no 20 micron size particles exist in the distribution, packing would be minimized. Similarly, with a particle size distribution of 75 to 125 microns, the mean particle size is 100 microns, and the largest interstitial space would be 100× 0.4=40 microns. Since no 40 micron particles exist in the distribution, packing would also be minimized. Therefore, if the ceramic particles are restricted to a narrow particle size range or equivalent size distribution, there will be a maximizing of the void volume into which the autogenous tissue can grow.

Other suitable particle size distribution ranges include 35 to 40 microns, 62 to 74 microns and 125 to 149 microns, however, any other correspondingly narrow ranges can also be used.

In contrast, where there is a wide particle size distribution, there is a greater tendency for the particles to become densely packed since the smaller particles tend to group or migrate into the spaces between the larger particles. This results in less interstitial space available between the particles for the autogenous tissue such as fibroblasts and chondroblasts to infiltrate and grow.

The tissue growth where the augmentation material has a wide particle size distribution is denser and harder, because of the packing effect which occurs between the large and small particles. In contrast, the use of particles equivalent in size, or having a narrow particle size range of uniformly distributed particles increases the intraparticle void volume. This enables a maximum amount of autogenous or three dimensional randomly oriented non-scar soft tissue in growth to infiltrate the space or interstices between the particles. The more interstitial space that is available makes it more likely that the subsequent autogenous tissue growth stimulated by the presence of the augmentation material into the matrix or scaffolding provided by the augmentation material will closely resemble the original tissue in the immediate vicinity or locus of augmentation.

The process of soft tissue augmentation can occur by injecting or implanting the biocompatible augmentation material comprising the desired particle sizes of the desired ceramic material into the tissue at the desired augmentation site to form a bleb or blister. The subsequent autogenous tissue growth into the matrix provided by the augmentation material will most closely resemble the surrounding tissue in texture and properties. This is in contrast to that which occurs using known state-of-the-art procedures, where, foreign body response is known to occur, typically with Teflon® augmentation where granulomas have been known to form.

Foreign body response is the body reaction to a foreign material. A typical foreign body tissue response is the appearance of polymorphonuclear leukocytes near the material followed by macrophages. If the material is nonbioreactive, such as silicone, only a thin collagenous encapsulation tissue forms. If the material is an irritant, inflammation will occur and this will ultimately result in granulation tissue formation. In the case of ceramic materials such as calcium hydroxyapatite, there is excellent biocompatibility resulting in tissue cell growth directly on the surface of the particles with a minimum of, or substantially no encapsulation.

Autogenous tissue is defined herein as any tissue at a specific defined location in the body, whose growth is stimulated by the presence of the matrix of the biocompatible augmentation material at the site where soft tissue augmentation is desired. Such autogenous tissue from augmentation in the area of the urethral sphincter would resemble existing tissue in the urethral sphincter. Autogenous tissue from augmentation in the larynx would resemble existing tissue in the glottis where the vocal apparatus of the larynx is located. Autogenous tissue from breast augmentation would resemble existing tissue in the mammaries, and so on. Autogenous tissue in the case of intradermal injections would resemble the dermis. In a similar manner, the augmentation material, by providing a three dimensional lattice can be used in surgical incisions or trauma to avoid linear, layered contractile scar formation.

As discussed above, the calcium hydroxyapatite particles used as the augmentation material are biocompatible and substantially non-resorbable. Thus, the soft tissue augmentation procedure is permanent. Moreover, the use of calcium hydroxyapatite does not require the strict rigorous precautions that are necessary when using other augmentation materials such as collagen which need refrigeration for storage, shipping and antigenicity testing.

The rounded, spherical smooth calcium hydroxyapatite particles enhance the biocompatibility to the autogenous tissue response into the particle matrix and substantially eliminates the potential for calcification. Jagged or irregular particles can irritate tissue and can cause calcification. In addition, surface porosity on the order of about 30 volume % or greater can also cause calcification because of the relative stability of the pores in the particles. Smooth round, substantially non-porous particles maintain movement in the tissue. Thus, the autogenous tissue grown in the particle matrix where movement is maintained, does not calcify. In contrast, the porous sections of the individual particles are stationary relative to the particle, thus tissue infiltration into the pores is not subject to movement and calcification can occur.

The particulate ceramic material can be suspended in a biocompatible, resorbable lubricant, such as a polysaccharide gel to improve the delivery of the augmentation material by injection to the tissue site where augmentation is desired. Suitable polysaccharides will be readily apparent to one skilled in the art. Polysaccharides that may be utilized in the present invention include, for example, any suitable polysaccharide within the following classes of polysaccharides: celluloses/starch, chitin and chitosan, hyaluronic acid, hydrophobe modified systems, alginates, carrageenans, agar, agarose, intramolecular complexes, oligosaccharide and macrocyclic systems. Examples of polysaccharides grouped into four basic categories include: 1. nonionic polysaccharides, including cellulose derivatives, starch, guar, chitin, agarose and. dextron; 2. anionic polysaccharides including cellulose derivatives starch derivatives, carrageenan, alginic acid, carboxymethyl chitin/chitosan, hyaluronic acid and xanthan; 3. cationic polysaccharides, including cellulose derivatives, starch derivatives guar derivatives, chitosan and chitosan derivatives (including chitosan lactate); and 4. hydrophobe modified polysaccharides including cellulose derivatives and alpha-emulsan. Preferred polysaccharides for use in the present invention include, for example, agar methylcellulose, hydroxypropyl methylcellulose, ethylcellulose, microcrystalline cellulose, oxidized cellulose, chitin, chitosan, alginic acid, sodium alginate, and xanthan gum.

The cellulose polysaccharide gels are particularly advantageous because of what can be referred to as their viscoelastic characteristics. Among these characteristics is that of shear thinning. That is, the cellulose polysaccharide gels will flow more readily as forces are applied thereto. This facilitates the ease of mixing when the solid granulate is added to the gel. The shear thinning also permits an easier delivery of the viscous material than would otherwise be the case. Another characteristic of the material is that it is elastic in that it tends to recover its initial shape after being deformed. This is highly significant because the elastic nature of the gel allows for the gel to suspend the augmentation material substantially indefinitely therefore achieving a substantially indefinite shelf life. Materials of relatively high density may be suspended by this gel. For example, calcium hydroxylapatite granulate, spherically shaped with diameters ranging from 75 to 125 micrometers, and with a density of 3.10 g/cc can be indefinitely suspended in a gel with a composition of 14.53 parts glycerin, 82.32 parts water, and 3.15 parts NaCMC.

The elastic characteristics of the gel in accordance with the present invention are further advantageous because the tissue augmentation material and the cellulose polysaccharide gel can be subjected to mixing to suspend the tissue augmentation material in the gel using conventional mixing apparatus without adverse impact on the gel carrier. That is, the gel carrier will not break down or lose its elastic properties. These processes are enhanced by the rate of recovery of gel elastic properties which occurs in a matter of seconds once the hydrated gel has been formed. This rapid recovery of shape due to the elasticity is also highly significant for placement and retention of the material when implanted into living tissue. The recovery of a more viscous characteristic, once the force of injection is removed, assists in the retention in place of the material, minimizing extravasation.

Any suitable solvent for the cellulose polysaccharide gel may be utilized in the present invention. For example, the gel may be an aqueous cellulose polysaccharide gel. Alternatively, the solvent may be an aqueous alcohol, including for example, glycerol, isopropyl alcohol, ethanol, and ethylene glycol, or mixtures of these. Other suitable solvents for the gel carrier will be apparent to one skilled in the art. Surfactants, stabilizers, pH buffers, and other additives may also be useful, as would be obvious to one skilled in the art. Pharmaceutically active agents, such as growth factors, antibiotics, analgesics, etc. could also be usefully incorporated and would be apparent to one skilled in the art.

In addition, while the present invention has been described herein with respect to a ceramic tissue augmentation material, the cellulose polysaccharide gel carrier of the present invention may also be utilized as a carrier for other tissue augmentation material. For example, the cellulose polysaccharide gel carrier of the present invention may be utilized as a carrier for non-ceramic tissue augmentation material such as, glass, polymethylmethacrylate, silicone, titanium and other metals, etc. Other suitable non-ceramic tissue augmentation material that may be suspended using the carrier of the present invention will be apparent to one skilled in the art.

The formulation of the gel will depend on a number of factors, including: 1) the molecular weight, degree of substitution, and other properties of the polysaccharide, 2) the solvent system employed, and 3) final properties required for the particular application of the material. In general, the ratio of cellulose polysaccharide to solvent can vary from about 0.5 to 10: 95.5 to 90. For example, in an 85:15 water:glycerin mixture, the ratio is preferably about 1.5 to 5: 98.5 to 95, and most preferably about 2.5 to 3.5: 97.5 to 96.5, respectively.

Preferably, the gel comprises water, glycerin and sodium carboxymethylcellulose. The gel enables the ceramic particles to remain in suspension without settling for an indefinite period of time until used, more specifically, at least about 6 months. Other suitable lubricant compositions known in the art can also be employed.

In general, the ratio of water (or other solvent, e.g. saline, Ringer's solution, etc.) to glycerin in the gel can vary from about 10 to 100:90 to 0, preferably about 20 to 90:80 to 10, and most preferably about 85:15, respectively.

The viscosity of the gel can vary from about 20,000 to about 350,000 centipoise, preferably about 150,000 to about 250,000 centipoise, and more preferably from greater than 200,000 to about 250,000 centipoise as measured with a Brookfield Viscometer with RU#7 spindle at 16 revolutions per minute (rpm) at 25° C. It has been found that with gel viscosities below about 20,000 centipoise the particles may not remain in suspension, and with gel viscosities above about 350,000 centipoise, the gel may become too viscous for convenient mixing.

In a preferred embodiment of the invention wherein the polysaccharide is sodium carboxymethylcellulose, the sodium carboxymethylcellulose included in the gel has a high viscosity. More specifically, the sodium carboxymethylcellulose preferably has a viscosity of about 1000 to 4000 centipoise, preferably about 2000 to 3000 centipoise, in a 1% aqueous solution per a procedure given in Hercules/Agualon Division Brochure 250-10F REV. 7–95 2M, "Sodium Carboxymethylcellulose Physical and Chemical Properties," pp. 26–27. The carboxymethylcellulose content can vary from about 0.25 to 5 weight %, preferably 2.50 to 3.50% of the combined (85 parts) water and (15 parts) glycerin in the gel.

The cellulose polysaccharide gel carrier of the present invention has been discussed in connection with the preferred sodium carboxymethylcellulose gel carrier. However, as discussed above, any suitable polysaccharide gel may be utilized for the carrier in accordance with the present invention, provided it suspends the tissue augmentation material homogeneously therein for a substantially indefinite period of time and possesses the shear thinning and elastic properties described above. More specifically, the polysaccharide gel carrier preferably has the following shear thinning and elastic properties: 1) a viscosity of between 1 and 5 million centipoise when stressed with a shear of 200 Pascals and a viscosity of 300,000 to 1 million cps when stressed with a shear of 500 Pa; 2) an elastic modulus, under a 100 Pa. maximum force measured at 1 hertz, of 50 to 1000 Pa.; 3) a ratio of viscous modulus to elastic modulus of 0.2 to 1.0, when measured under a 100 Pa. maximum force at 1 hertz; 4) a recovery of deformation of 5 to 75% after being subjected to a deformation force of 100 Pa for 120 seconds; and, 5) a majority of the recovery of the deformation in (4) should occur in 2 to 10 seconds. The measurements described above can be conducted with a controlled stress rheometer, e.g. a Haake RS100 with a 2 cm. parallel plate, operating in stress ramp, oscillatory, and creep/recovery modes. The actual values of the shear thinning and elastic properties described above will depend on the intended application and properties (e.g. size, density, etc.) of a dispersed particulate.

In the tissue augmentation material and method of the present invention, other polysaccharides can also be included or used separately such as cellulose, agar methylcellulose, hydroxypropyl methylcellulose, ethylcellulose, microcrystalline cellulose, oxidized cellulose, chitin, chitosan, alginic acid, sodium alginate, xanthan gum and other equivalent materials.

Unexpectedly, formulating the augmentation particles of the present invention, particularly the calcium hydroxyapatite with sodium carboxymethylcellulose, provides a change in the surface morphology of the particles which is believed to enhance the physical and biocompatible properties of the material.

The glycerin in the preferred formulation provides several advantages. First, the composition is more lubricious when glycerin is present. Second, for a given level of polysaccharide gel former, the viscosity is substantially enhanced with some glycerin relative to a pure aqueous gel. Third, the presence of the glycerin minimizes moisture loss of the gel by dessication.

The gel is prepared by mixing the gel components at ambient conditions until all components are in solution. It is preferable to combine the glycerin and NaCMC components together first until a thoroughly mixed solution is obtained. The glycerin/NaCMC solution is then mixed together with the water until all components are in solution to form the gel. After the gel components have been thoroughly mixed, the gel is allowed to set for a minimum of 4 hours, after which viscosity readings are taken to ensure that the gel has the desired viscosity.

While any lubricant or carrier can be employed, it has been found that certain materials, e.g., polysorbate surfactants, pectin, chondroitin sulfate and gelatin, are not able to suspend the ceramic particles for an indefinite amount of time and allow further processing or be as easy to inject in the same manner as the preferred sodium carboxymethylcellulose. Thus, the sodium carboxymethylcellulose materials are preferred.

The preferred polysaccharide gel is biocompatible and able to maintain the particles of ceramic material in what amounts to a substantially permanent state of suspension so that the ceramic particulate/gel composition comprising the augmentation material does not require mixing before use. As already noted, the lubricious nature of the polysaccharide gel reduces the frictional forces generated by transferring the augmentation material from a syringe by injection into the tissue site.

In addition, the polysaccharides do not generate an antigenic response as do products containing amino acids. The polysaccharide gel is readily sterilizable and stable at ambient conditions and does not need refrigeration for storage and shipment, in contrast to systems used with collagen containing materials.

Sterilization is ordinarily accomplished by autoclaving at temperatures on the order of about 115° C. to 130° C., preferably about 120° C. to 125° C. for about 30 minutes to 1 hour. Gamma radiation is unsuitable for sterilization since it tends to destroy the gel. It has also been found that sterilization generally results in reduction of its viscosity. However, this does not adversely affect the suspension and therefore the extrusion force of the augmentation material through a syringe, nor does it affect the ability of the gel to hold the calcium hydroxyapatite particles in suspension, as long as the prescribed viscosity ranges for the gel are maintained.

After injection of the augmentation material into the tissue, the polysaccharide gel is harmlessly resorbed by the tissue, leaving the non-resorbable calcium hydroxyapatite matrix in place in the particular area or bolus, where it has been found to remain without migrating to other areas of the body. It generally takes an average of about 2 weeks for the polysaccharide to completely resorb.

Figure 2:
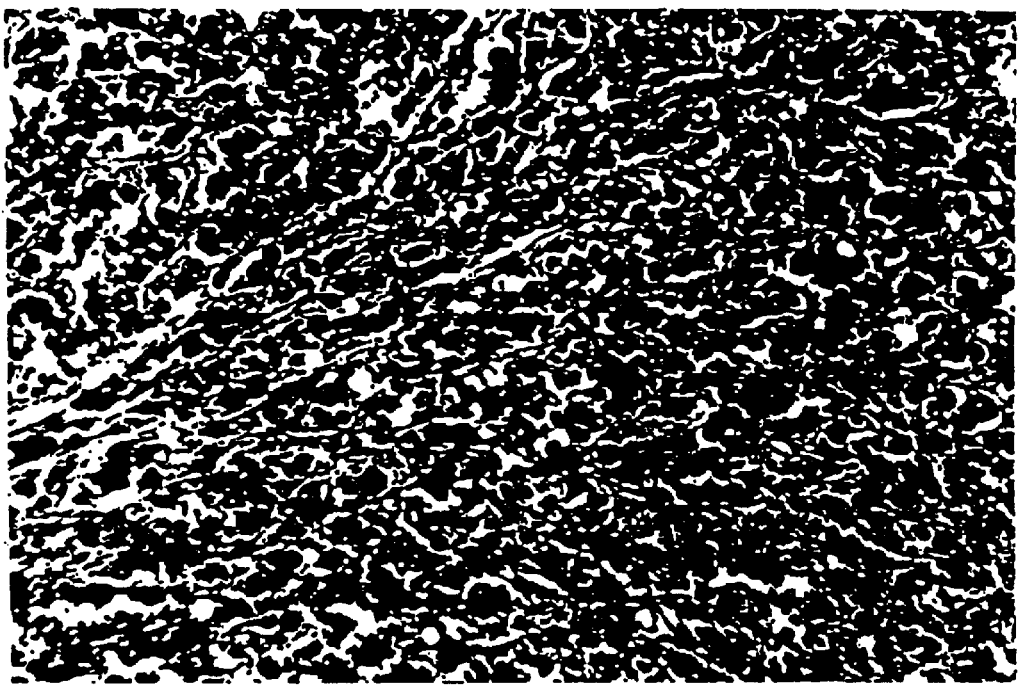
FIG. 2 is a photomicrograph of a histological section of rabbit tissue at 50× magnification showing fibroblastic infiltration.

FIG. 2 shows a histological section of rabbit tissue at 50× magnification which has been infiltrated with autogenous three dimensional, randomly oriented, non-scarring soft muscle tissue as a result of an injection of calcium hydroxyapatite particles having a uniform particle size distribution of 38 to 63 microns. The photomicrograph shows growth after 12 weeks. The histological section also demonstrates the biocompatibility of the calcium hydroxyapatite as the cells grow on the surface of the particles with minimal or substantially no foreign body response.

It has been found that the amount of calcium hydroxyapatite particles in the augmentation material can vary from about 15% to 50% by volume, and preferably about 25% to 47.5% and most preferably about 35% to 45% by volume of the total augmentation material, comprising the gel and the ceramic particles.

Preparations having above 50 volume % ceramic particles become viscous and care should be taken as to the selection of injection apparatus. As a lower limit the augmentation material of this invention should obviously contain a sufficient volume of ceramic particles to provide an effective base for autogenous tissue growth. For most applications this is at least 15 volume %. By maintaining a volume % of about 35 to 45%, a correction factor of about 1:1 can be achieved, that is, the volume of autogenous tissue growth is roughly equivalent to the volume of particles introduced and shrinkage or expansion at the site of the soft tissue augmentation does not generally occur.

Also, within these parameters, the augmentation material can easily be injected through an 18 gauge or smaller syringe intradermally or subcutaneously. Because of the reduced frictional forces necessary to deliver the biocompatible augmentation material by injection to the desired tissue site, the size of the syringe used to transfer or inject the biocompatible augmentation material can be significantly reduced. This substantially eliminates the possibility of creating a needle trail through which leakage of the augmentation material from the injection site can occur after withdrawing the injection needle. Thus, the syringes used to inject the augmentation material can have reduced openings of less than 1,000 microns in diameter to a minimum of about 178 microns or less.

For example, an 18 gauge syringe having a diameter of about 838 microns, or a 20 gauge syringe having a diameter of about 584 microns, or a 22 gauge syringe having a diameter of about 406 microns, and even a 28 gauge syringe having a diameter of about 178 microns can be used, depending on the tissue site where augmentation is needed.

The lubricious suspension of augmentation material is prepared by simply mixing the desired amount of ceramic particles with the lubricious gel until a uniform, homogeneous suspension is reached. The consistency of the ceramic particles suspended in the lubricious gel is comparable to strawberry preserves, wherein the seeds and other solid parts of the strawberry, for all practical purposes, are comparable to the ceramic particles and remain substantially permanently suspended in the jelly preserve matrix.

The suspension of ceramic material in the lubricious gel is so stable, that centrifugation at forces on the order of 500 g's, that is, 500 times the force of gravity generally do not affect the stability of the suspension or cause it to settle out. The tendency, if any, for particles to settle out over a period of time would appear more likely to occur with the larger particle sizes on the order of 125 microns or larger. Thus, remixing the augmentation material at the time of injection or implantation is ordinarily not necessary. In addition, the polysaccharide gel lubricates the suspended ceramic particles so that the injection force on the syringe can be minimized when injecting the augmentation material.

Tissue augmentation material in accordance with the present invention is particularly advantageous in the treatment of osteoporosis or related pathologies in, for example, the femur, or osseous defects due to trauma or surgical incision. The advantages of this material in these applications include biocompatibility, ease of application, and a superior result to other materials currently employed.

Specifically, because the material can be injected through fine catheters and needles, small incision sites such as less than a 4.5 mm hole in the bone site may be used, resulting in minimizing the immediate loss of bone trabeculae—the opposite of the intended longer term result. Because of the smaller needle required for using tissue augmentation material in accordance with the present invention, the hole diameter could be greatly reduced and the depth could also be greatly reduced.

Particles are held together in the present invention for some time by the gel carrier, even in a liquid environment. In an osseous site, the gel would provide a means of "fixing" the particles for a period of time.

Furthermore, because the particulate is relatively small, it is distributed more widely in the site of interest via injection.

The viscosity of the gel carrier could be tailored to produce either a "thin, runny" consistency media or a "thick, robust" consistency, as desired. This could be done by modifying the content of the other components of the composition including, for example, glycerin and sodium carboxymethylcellulose.

The particle size of the ceramic particulate in the tissue augmentation material could be reduced for this application. That is, material which could be used would be a 37–63 μm CaHA particulate. The main advantage of a larger size range of particle sizes in soft tissue is to ensure a lack of migration due to cellular mechanisms that could transport the particulate to distant organ sites. The chance of this occurring, however, would be greatly reduced for particulate contained, for example, within a trabecular bone cavity. Also, the fact that CaHA is known to bond to bone further reduces concern of migration.

Also, it has been discovered that tissue augmentation material in accordance with the present invention can be the basis for a unique material useful in implant applications. Specifically, it has been discovered that if tissue augmentation material in accordance with the invention is allowed to dry by exposure to air, it developed some surprising properties. If extruded from a syringe, either directly or through a needle or catheter, a "string" of particles with surprising cohesion and flexibility would result after exposure to air. It was apparent that the material was substantially dehydrated and it is possible to form the material in various shapes or into sheets, as desired. The material may be molded and shaped like clay or carved into shape with appropriate instruments to prepare a preform for implantation. The advantages of this material include cohesion, moldability, and the high concentration of particulate per unit volume.

The following examples show specific embodiments of the invention. All parts and percentages are by weight unless otherwise noted.

EXAMPLES

Example 1

Preparation of the Gel

A mixture of 15% glycerin, 85% water, (based on the combined weight of the water and glycerin) and 3.25% NaCMC (again based on the total of the liquid components) is prepared in the following manner:

9.303 g of glycerin and 2.016 g of NaCMC are combined in a vessel. The mixture is then slowly added to 52.718 g of agitating water in a container large enough for batch size and allowed to mix, utilizing an electric mixer, for 30 minutes at a medium speed. The gel is allowed to set for a minimum of four hours.

Example 2

Preparation of the Augmentation Composition

Aqueous glycerin/NaCMC gel (44.04 g, prepared in Example 1) are placed in a mixing container large enough for batch size. Smooth, rounded substantially spherical CaHA particles (55.99 g) having a uniform particle size of 75 to 125 microns are thoroughly blended, utilizing an electric mixer, for five minutes at a low speed until all the particles are homogeneously distributed in a uniform suspension in the gel. The blended material is packaged in 3 cc polysulfone cartridges and sterilized in an autoclave for 60 minutes at 121° C.

Example 3

Properties of Augmentation Composition

Figure 3:
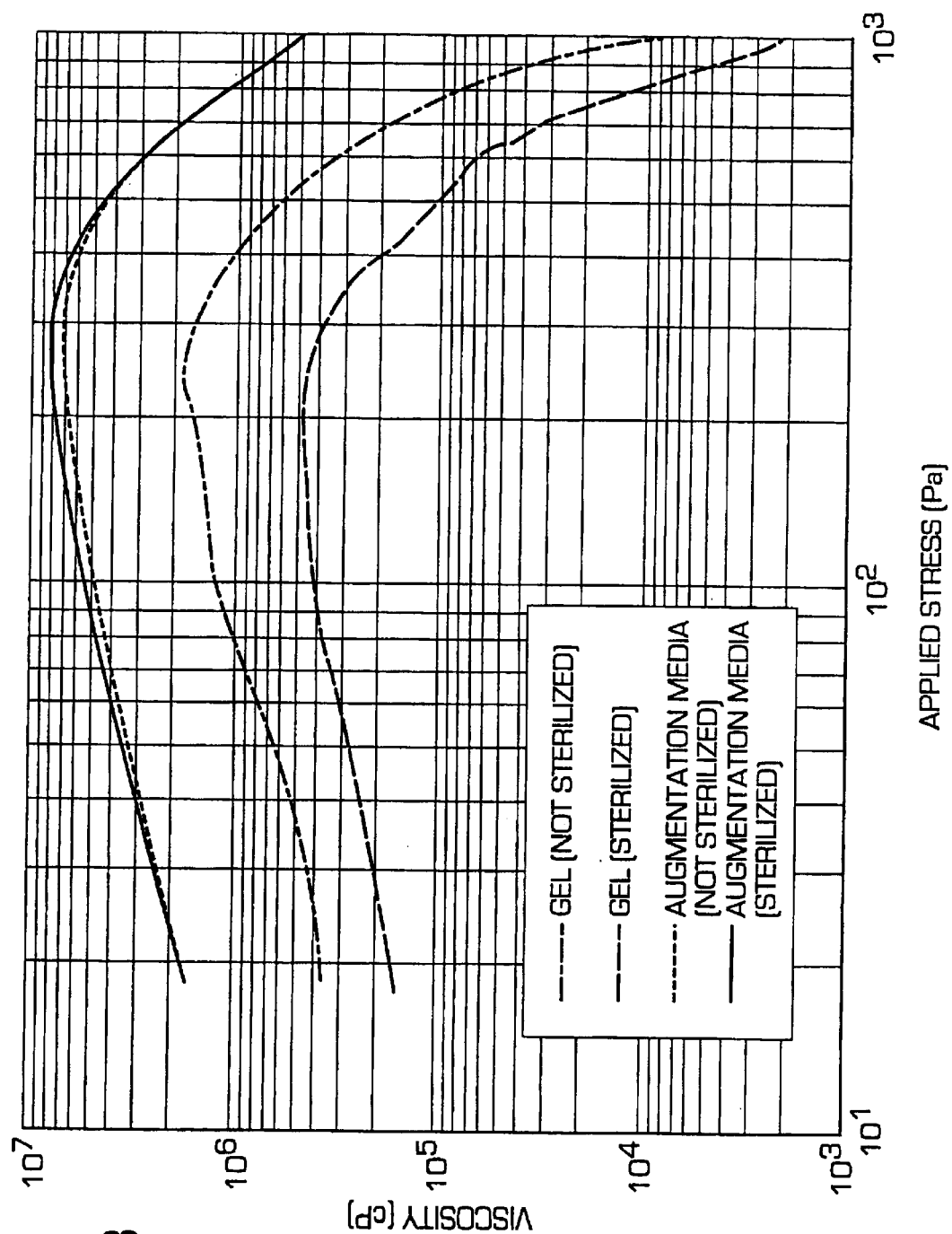
FIG. 3 is a graph of the viscosity of the gel and augmentation media both before and after sterilization.

The gel as prepared in Example 1, and the augmentation medium as prepared in Example 2 are examined by means of a parallel plate rheometer (Haake RS100). Testing includes the measurement of Theological properties as a function of applied stress (stress ramp), deformation at constant stress followed by recovery at 0 stress (creep/recovery), and the measurement of the complex modulus using an oscillating stress within the viscoelastic limit of the composition (frequency sweep). Outcomes demonstrate that the behavior of the gel and augmentation composition, both before and after sterilization, is the same. For example, this is demonstrated in FIG. 3, which shows the viscosity of the gel and augmentation material before and after sterilization as a function of applied stress from 10 to 1000 Pascals. The shape of the curves are similar and demonstrate the shear thinning characteristic of this material. Other measured values are given in the following table. The viscosity is determined at 500 Pa in a stress ramp measurement. The elastic modulus is determined under an oscillating force of 100 Pa at 1 hertz. The ratio of the inelastic modulus to elastic modulus, tan δ, is determined under an oscillating force of 100 Pa at 1 hertz. The maximum deflection, γ max, is determined after 120 seconds of a constant 100 Pa applied stress. The % Recovery is determined after a relaxation of 200 seconds following 120 seconds of a constant 100 Pa applied stress.

TABLE 1

Rheological results of gel and augmentation materials taken on a Haake RS100 control stress rheometer using 2 cm. parallel plates.

|  | As Prepared Gel | As Prepared Augmentation Composition | Sterilized Augmentation Composition |
|---|---|---|---|
| Viscosity (Cp) @ 500 Pa stress | 603,000 | 4,610,000 | 4,340,000 |
| Elastic Modulus (100 Pa @ 1 Hz) | 408 | 2520 | 2684 |
| tan δ (100 Pa @ 1 Hz) | 0.461 | 0.453 | 0.429 |
| γ max | 2.227 | 0.367 | 0.345 |
| % Recovery | 44.99 | 45.50 | 46.96 |

Example 4

Preparation of the Gel

A mixture of 25% glycerin, 75% water, and 2.25% NaCMC (based on the combined weight of the water and glycerin) is prepared in the following manner:

87.90 g of glycerin and 7.91 g of NaCMC are combined in a vessel large enough to mix the total mass. The mixture is then slowly added to 263.71 g of agitating water in a container large enough for batch size and allowed to mix, utilizing an electric mixer, for 30 minutes at a medium speed. The gel is allowed to set for a minimum of four hours.

Example 5

Preparation of the Augmentation Composition

Aqueous glycerin/NaCMC gel (38.52 g, prepared in Example 1) are placed in a mixing container large enough for batch size, Smooth, rounded substantially spherical CaHA particles (74.86 g) having a uniform particle size of 37 to 63 microns are thoroughly blended, utilizing an electric mixer, for five minutes at a low speed until all the particles are homogeneously distributed in a uniform suspension in the gel.

Example 6

In most instances it takes relatively little force to inject or extrude the augmentation composition, comprising the polysaccharide gel/particulate calcium hydroxyapatite suspension, into the air since there is relatively little resistance. However, greater forces were necessary to inject the augmentation composition into tissue, and this force is significantly influenced by the shape of the particulate material. This was exemplified by preparing sterilized suspensions of polysaccharide gel made of 75% water, 25% glycerin, and 2.25% sodium carboxymethylcellulose (based on the combined weight of the water and glycerin) with various volume percents of calcium hydroxyapatite particles having different shapes, following the procedure of Example 2. The thus prepared suspensions were placed in standard 3 cubic centimeter syringes. The force applied to the plunger to extrude the polysaccharide gel/particulate suspension at a rate of one inch per minute through an 18 gauge needle was then measured. The force was also measured with the needle inserted into turkey gizzard tissue as an analogy as it would be used clinically. The spray dried particles of calcium hydroxyapatite, regardless of their shape, had a smooth, uniform appearance under microscopic examination at 40× magnification. The particles were uniformly distributed within the range of particle sizes. The results are tabulated in Table 2, which follows:

TABLE 2

Calcium Hydroxyapatite Particles in the Gel

| Size, Microns | Particle Shape | Volume. % Solids | Force, lbs Air | Force, lbs Tissue |
|---|---|---|---|---|
| 38 to 63 | Spherical/Smooth | 35 | 4.5 | 6.0 |
| 38 to 63 | Spherical/Smooth | 40 | 5.9 | 7.2 |
| 38 to 63 | Irregular | 40 | 8.0* | 9.6* |
| 74 to 100 | Irregular/Smooth | 37 | 5.5 | >30 |
| 74 to 100 | Irregular/Smooth | 41 | >30 | >30 |
| 74 to 100 | Spherical/Smooth | 42 | 4.8 | 5.5 |

*Average. Inconsistent results due to complete obstruction of needle that sporadically occurred during the tests, requiring replacement of needle.

This data correlated with animal experimentation where it was not possible to inject irregular particles into tissue even when the percent solids were reduced below 25 volume % or a 16 gauge needle was used.

Example 7

Sterilized samples of polysaccharide gel/particulate calcium hydroxyapatite suspensions were prepared using a series of designated particle size ranges. The distribution of particles was uniform within each range of particle sizes. The particles were smooth, round calcium hydroxyapatite, and the gel had the same constituency as Example 1. The calcium hydroxyapatite particles occupied 36 volume % of the suspension. The extrusion force into the air for each suspension containing each designated range of particle sizes was measured using a standard 3 cubic centimeter syringe in the same manner as in Example 6. The results are tabulated in Table 3, which follows, and demonstrate that little difference in the extrusion force occurs as the particle size increases, as long as the particle sizes are uniform and maintained in a narrow distribution range.

TABLE 3

| Size Distribution, microns | Extrusion Force, lbs |
|---|---|
| 40–60 | 2.3 |
| 62–74 | 2.0 |
| 40–74 | 2.6 |
| 82–100 | 2.3 |
| 100–125 | 2.2 |
| 125–149 | 2.4 |
| 100–149 | 2.4 |

Example 8

Sodium carboxymethylcellulose, water and glycerin in various weight percents were formulated into four different gels following the procedure of Example 1, except for the use of different proportions. Each gel was then blended with about 40 volume % calcium hydroxyapatite particles having a distribution of 38 to 63 microns. The gel/particle blends were then placed in standard 3 cubic centimeter syringes fitted with 18 gauge, 20 gauge and 22 gauge needles. The extrusion force of the blend into the air was measured in the same manner as in Example 3. The results appear below in Table 4.

TABLE 4

| Weight % | | | Force, lbs | | |
|---|---|---|---|---|---|
| % NaCMC* | Glycerin | Water | 18 gauge | 20 gauge | 22 gauge |
| 1.0 | 60 | 40 | 3.6 | 6.4 | 7.7 |
| 1.5 | 50 | 50 | 4.0 | 5.8 | 8.2 |
| 2.0 | 30 | 70 | 4.1 | 6.3 | 7.7 |
| 2.0 | 40 | 60 | 4.8 | 7.0 | 9.2 |

*Sodium carboxymethylcellulose. Weight % of sodium carboxymethylcellulose based on total weight of glycerin and water.

Example 9

Preparation of the Augmentation Composition Using Polystyrene Microbeads

A gel consisting of 4.93% glycerin, 93.60% water, and 1.48% NaCMC was prepared by methods described in Example 1. Spherical polystyrene beads (12.79 g), having a particle size range of 100 to 500 microns are thoroughly blended, utilizing an electric planetary mixer, for five minutes at a low speed until all the particles are homogeneously distributed in a uniform suspension in 28.43 grams of gel. The polystyrene beads have a density of 1.07 g/cc as measured by helium pycnometry. The blended material is packaged in 10 cc polypropylene syringe cartridges and sterilized in an autoclave for 60 minutes at 121° C. The polystyrene beads remained homogeneously distributed within the gel carrier. Rheologic properties were measured as described in Example 3. The viscosity is determined at 100 Pa in a stress ramp measurement. The elastic modulus is determined under an oscillating force of 20 Pa at 1 hertz. The ratio of the inelastic modulus to elastic modulus, tan δ, is determined under an oscillating force of 20 Pa at 1 hertz. The maximum deflection, γ max, is determined after 120 seconds of a constant 10 Pa applied stress. The % Recovery is determined after a relaxation of 200 seconds following 120 seconds of a constant 10 Pa applied stress. Results are shown in Table 5.

TABLE 5

Rheological results of gel and polystyrene augmentation material taken using a Haake RS100 control stress rheometer using 2 cm. parallel plates.

|  | As Prepared Gel | As Prepared Augmentation Composition | Sterilized Augmentation Composition |
| --- | --- | --- | --- |
| Viscosity (Cp) @ 100 Pa stress | 2,050 | 47,900 | 9,630 |
| Elastic Modulus (20 Pa @ 1 Hz) | 11 | 31 | 16 |
| tan δ (20 Pa @ 1 Hz) | 1.348 | 1.320 | 2.067 |
| γ max, (@ 10 Pa.) | 27.406 | 5.717 | 47.873 |
| % Recovery | 22.4 | 23.4 | 1.6 |

Example 10

Preparation of the Augmentation Composition Using Polymethylmethacrylate Microbeads A gel consisting of 9.80% glycerin, 88.24% water, and 1.96% NaCMC was prepared by methods described in Example 1. Spherical polymethylmethacrylate beads (12.78 g), having a uniform particle size of 100 to 180 microns are thoroughly blended, utilizing an electric planetary mixer, for five minutes at a low speed until all the particles are homogeneously distributed in a uniform suspension in 28.84 grams of gel. The polymethylmethacrylate beads have a density of 1.21 g/cc as measured by helium pycnometry. The blended material is packaged in 10 cc polypropylene syringe cartridges and sterilized in an autoclave for 60 minutes at 121° C. The polymethylmethacrylate beads remain homogeneously distributed within the gel carrier. Rheologic properties were measured as described in Example 6. The viscosity is determined at 100 Pa in a stress ramp measurement. The elastic modulus is determined under an oscillating force of 20 Pa at 1 hertz. The ratio of the inelastic modulus to elastic modulus, tan δ, is determined under an oscillating force of 20 Pa at 1 hertz. The maximum deflection, γ max, is determined after 120 seconds of a constant 20 Pa applied stress. The % Recovery is determined after a relaxation of 200 seconds following 120 seconds of a constant 20 Pa applied stress. Results are shown in Table 3.

TABLE 6

Rheological results of gel and polymethylmethacrylate augmentation material taken using a Haake RS100 control stress rheometer using 2 cm. parallel plates.

|  | As Prepared Gel | As Prepared Augmentation Composition | Sterilized Augmentation Composition |
| --- | --- | --- | --- |
| Viscosity (Cp) @ 100 Pa stress | 58,700 | 482,000 | 22,200 |
| Elastic Modulus (20 Pa @ 1 Hz) | 58 | 212 | 42 |
| tan δ (20 Pa @ 1 Hz) | 0.785 | 0.705 | 1.934 |
| γ max | 2.895 | 1.111 | 0.211 |
| % Recovery | 53.1 | 48.2 | 20.9 |

Example 11

Preparation of the Augmentation Composition Using Glass Microbeads

A gel consisting of 14.56% glycerin, 82.52% water, and 2.91% NaCMC was prepared by methods described in Example 1. Spherical glass beads (30.42 g), having a uniform particle size of 30 to 90 microns are thoroughly blended, utilizing an electric planetary mixer, for five minutes at a low speed until all the particles are homogeneously distributed in a uniform suspension in 29.27 grams of gel. The glass beads have a density of 2.54 g/cc as measured by helium pycnometry. The blended material is packaged in 10 cc polypropylene syringe cartridges and sterilized in an autoclave for 60 minutes at 121° C. The glass beads remain homogeneously distributed within the gel carrier. Rheologic properties were measured as described in Example 3. The viscosity is determined at 500 Pa in a stress ramp measurement. The elastic modulus is determined under an oscillating force of 100 Pa at 1 hertz. The ratio of the inelastic modulus to elastic modulus, tan δ, is determined under an oscillating force of 100 Pa at 1 hertz. The maximum deflection, γ max, is determined after 120 seconds of a constant 100 Pa applied stress. The % Recovery is determined after a relaxation of 200 seconds following 120 seconds of a constant 100 Pa applied stress. Results are shown in Table 7. The sterilized augmentation material was filled into 3 cc syringe cartridges and extruded through 3.5 inch 20 gauge spinal needles. The average extrusion force was 14.63 lbs. with a standard deviation of 0.09 lbs.

TABLE 7

Rheological results of gel and glass augmentation material taken using a Haake RS100 control stress rheometer using 2 cm. parallel plates.

|  | As Prepared Gel | As Prepared Augmentation Composition | Sterilized Augmentation Composition |
| --- | --- | --- | --- |
| Viscosity (Cp) @ 500 Pa Stress | 135,000 | 803,000 | 569,000 |
| Elastic Modulus (100 Pa @ 1 Hz)) | 256 | 699 | 570 |
| tan δ (100 Pa @ 1 Hz) | 0.545 | 0.557 | 0.692 |
| γ max | 4.302 | 1.195 | 3.259 |
| % Recovery | 36.3 | 37.7 | 24.7 |

Example 12

Preparation of the Aucrmentation Composition Using Stainless Steel Microbeads

A gel consisting, of 4.76% glycerin, 90.48% water, and 4.76% NaCMC was prepared by methods described in Example 1. The mixing time was extended from 30 minutes to one hour for this formulation. Spherical stainless steel beads (95.19 g), having a uniform particle size of 60 to 125 microns are thoroughly blended, utilizing an electric planetary mixer, for five minutes at a low speed until all the particles are homogeneously distributed in a uniform suspension in 28.69 grams of gel. The stainless steel beads have a density of 7.93 g/cc as measured by helium pycnometry. The blended material is packaged in 10 cc polypropylene syringe cartridges and sterilized in an autoclave for 60 minutes at 121° C. The stainless steel beads remain homogeneously distributed within the gel carrier. Rheologic properties were measured as described in. Example 3. The viscosity is determined at 500 Pa in a stress ramp measurement. The elastic modulus is determined under an oscillating force of 100 Pa at 1 hertz. The ratio of the inelastic modulus to elastic modulus, tan δ, is determined under an oscillating force of 100 Pa at 1 hertz. The maximum deflection, γ max, is determined after 120 seconds of a constant 100 Pa applied stress. The % Recovery is determined after a relaxation of 200 seconds following 120 seconds of a constant 100 Pa applied stress. Results are shown in Table 8. The sterilized augmentation material was filled into 3 cc syringe cartridges and extruded through 3.5 inch 20 gauge spinal needles. The average extrusion force was 30.84 lbs with a standard deviation of 0.37 lbs.

TABLE 8

Rheological results of gel and stainless steel augmentation material taken on a Haake RS100 control stress rheometer using 2 cm. parallel plates.

|  | As Prepared Gel | As Prepared Augmentation Composition | Sterilized Augmentation Composition |
|---|---|---|---|
| Viscosity (Cp) @ 500 Pa stress | 8,150,000 | 42,400,000 | 23,600,000 |
| Elastic Modulus (100 Pa @ 1 Hz) | 1663 | 8411 | 5085 |
| tan δ (100 Pa @ 1 Hz) | 0.335 | 0.366 | 0.400 |
| γ max | 0.336 | 0.110 | 0.197 |
| % Recovery | 62.8 | 64.5 | 54.3 |

Example 13

Preparation of the Augmentation Composition Using a Xanthan Gum Gel Former

A gel consisting of 13.8 parts glycerin, and 78.2 parts water, and 8 parts xanthan gum polysaccharide was prepared by methods described in Example 1. The viscosity of the gel, measured using a Brookfield Rheometer, was 51,250 cps. Calcium hydroxylapatite granulate in a range of 75 to 125 microns in diameter are thoroughly blended, utilizing an electric planetary mixer, for five minutes at a low speed until all the particles are homogeneously distributed in a uniform suspension in of gel. The blended material is packaged in polypropylene syringe cartridges and sterilized in an autoclave for 60 minutes at 121° C. The hydroxlyapatite particulate remained homogeneously distributed within the gel carrier. Centrifugation of the cartridges in a IEC Clinical centrifuge, Model OM428, at a force of 1016×g for 5 minutes did not result in a settling of the particulate in the gel carrier. (This result suggests that the particulated will not settle even over an extended period of time as the elastic limit of the gel will not be exceeded.) The augmentation material was extruded from the syringe cartridges through 1.5 inch long 18 gauge needles. The force required was 3.90 lbs.

Example 14

Preparation of the Augmentation Composition Using a Xanthan Gum Gel Former and Isopropylacohol A gel consisting of 64.4 parts isopropyl alcohol, and 27.6 parts water, and 8 parts xanthan gum polysaccharide was prepared by methods described in Example 1. The viscosity of the gel, measured using a Brookfield Rheometer, was 37,500 cps. Calcium hydroxylapatite granulate in a range of 75 to 125 microns in diameter are thoroughly blended, utilizing an electric planetary mixer, for five minutes at a low speed until all the particles are homogeneously distributed in a uniform suspension in of gel. The blended material is packaged in polypropylene syringe cartridges and sterilized in an autoclave for 60 minutes at 121° C. The hydroxylapatite particulate remained homogeneously distributed within the gel carrier. Centrifugation of the cartridges in a IEC Clinical centrifuge, Model OM428, at a force of 1016×g for 5 minutes did not result in a settling of the particulate in the gel carrier. (This result suggests that the particulated will not settle even over an extended period of time as the elastic limit of the gel will not be exceeded.) The augmentation material was extruded from the syringe cartridges through 1.5 inch long 18 gauge needles. The force required was 7.34 lbs.

Example 15

The gel is prepared in accordance with Example 1, and the augmentation medium is prepared in accordance with Example 2. The patient is then appropriately anesthetized and a hole (greater in diameter than an 18 gauge needle) is then drilled with an entry point in the soft cancellous part of the greater trochanter into the neck, head and trochanteric region of the femur. An 18 gauge needle 3.5 inches long is connected to the syringe containing the augmentation media using the Luer lock connection. The augmentation media is then injected through the hole in the bone. Sufficient material is injected to serve as a scaffold for bone growth between the particles creating osseous formation and strengthening of the trochanter and the femoral head of the femur and thus reducing the risk of fracture.

Although the present invention has been described in connection with preferred embodiments thereof, many other variations and modifications and other uses will become apparent to those skilled in the art without departing from the scope of the invention. It is preferred, therefore, that the present invention not be limited by the specific disclosure herein, but only by the appended claims.

What is claimed is:

1. A biocompatible, resorbable, lubricous carrier for suspending a biomaterial in a tissue augmentation material, comprising a polysaccharide gel having a viscosity between about 20,000 centipoise to about 350,000 centipoise, wherein the polysaccharide gel maintains the biomaterial homogeneously suspended in the tissue augmentation material prior to augmentation of a desired tissue site and during introduction of the tissue augmentation material to the desired site.

2. The carrier according to claim 1, wherein the polysaccharide gel is an aqueous polysaccharide gel.

3. The carrier according to claim 1, wherein the polysaccharide gel comprises a polysaccharide selected from the group consisting of a cellulose polysaccharide, starch, chitin, chitosan, hyaluronic acid, hydrophobe modified polysaccharide, an alginate, a carrageenan, agar, agarose, an intramolecular complex of a polysaccharide, an oligosaccharide and a macrocyclic polysaccharide.

4. The carrier according to claim 3, wherein the polysaccharide gel comprises a cellulose polysaccharide.

5. The carrier according to claim 4, wherein the cellulose polysaccharide is selected from the group consisting of sodium carboxymethylcellulose, agar methylcellulose, hydroxypropyl methylcellulose, ethylcellulose, microcrystalline cellulose and oxidized cellulose.

6. The carrier according to claim 5, wherein the cellulose polysaccharide is sodium carboxymethylcellulose.

7. The carrier according to claim 1, wherein the polysaccharide gel comprises a solvent selected from the group consisting of water and aqueous alcohol.

8. The carrier according to claim 7, wherein the aqueous alcohol is selected from the group consisting of aqueous glycerol, aqueous isopropyl alcohol, aqueous ethanol, aqueous ethylene glycol and mixtures thereof.

9. The carrier according to claim 2, further comprising glycerin.

10. The carrier according to claim 9, wherein water and the glycerin are present in the aqueous polysaccharide gel in a ratio of from about 20 to 90:80 to 10.

11. The carrier according to claim 10, wherein the water and the glycerin are present in the gel in a ratio of about 85:15.

12. The carrier according to claim 1, wherein the biomaterial is selected from the, group consisting of a ceramic, a plastic and a metal.

13. The carrier according to claim 12, wherein the biomaterial is a ceramic.

14. The carrier according to claim 13, wherein the ceramic comprises rounded, substantially spherical, biocompatible, substantially non-resorbable, finely divided ceramic particles.

15. The carrier according to claim 14, wherein the ceramic particles are selected from the group consisting of calcium phosphate particles, calcium silicate particles, calcium carbonate particles and alumina particles.

16. The carrier according to claim 12, wherein the ceramic particles are calcium phosphate particles.

17. The carrier according to claim 16, wherein the calcium phosphate particles are selected from the group consisting of calcium hydroxyapatite particles, tetracalcium phosphate particles, calcium pyrophosphate particles, a tricalcium phosphate particles, octacalcium phosphate particles, calcium fluorapatite particles, calcium carbonate apatite particles and mixtures thereof.

18. The carrier according to claim 17, wherein the calcium phosphate particles are calcium hydroxyapatite particles.

19. The carrier according to claim 1, wherein the desired tissue site is an osseous site.

20. The carrier according to claim 19, wherein the desired tissue site is an osseous site in a state of osteoporosis.

21. A biocompatible composition for augmenting tissue, comprising a biomaterial for augmenting a desired tissue site and a biocompatible, resorbable, lubricous carrier for the biomaterial, the carrier comprising a polysaccharide gel having a viscosity between about 20,000 centipoise to about 350,000 centipoise, wherein the carrier maintains the biomaterial homogeneously suspended in the biocompatible composition prior to augmentation of a desired tissue site and during introduction of the biocompatible composition to the desired site.

22. The composition according to claim 21, wherein the polysaccharide gel is an aqueous polysaccharide gel.

23. The carrier according to claim 21, wherein the polysaccharide gel comprises a polysaccharide selected from the group consisting of a cellulose polysaccharide, starch, chitin, chitosan, hyaluronic acid, hydrophobe modified polysaccharide, an alginate, a carrageenan, agar, agarose, an intramolecular complex of a polysaccharide, an oligosaccharide and a macrocyclic polysaccharide.

24. The composition according to claim 23, wherein the polysaccharide gel comprises a cellulose polysaccharide.

25. The composition according to claim 24, wherein the cellulose polysaccharide is selected from the group consisting of sodium carboxymethylcellulose, agar methylcellulose, hydroxypropyl methylcellulose, ethylcellulose, microcrystalline cellulose and oxidized cellulose.

26. The composition according to claim 25, wherein the cellulose polysaccharide is sodium carboxymethylcellulose.

27. The composition according to claim 21, wherein the polysaccharide gel comprises a solvent selected from the group consisting of water and aqueous alcohol.

28. The composition according to claim 27, wherein the aqueous alcohol is selected from the group consisting of aqueous glycerol, aqueous isopropyl alcohol, aqueous ethanol, aqueous ethylene glycol and mixtures thereof.

29. The composition according to claim 22, further comprising glycerin.

30. The composition according to claim 29, wherein water and the glycerin are present in the aqueous polysaccharide gel in a ratio of from about 20 to 90:80 to 10.

31. The composition according to claim 30, wherein the water and glycerin are present in the aqueous polysaccharide gel in a ratio of about 85:15.

32. The composition according to claim 21, wherein the biomaterial is selected from the group consisting of a ceramic, a plastic and a metal.

33. The composition according to claim 32, wherein the biomaterial is a ceramic.

34. The composition according to claim 33, wherein the ceramic comprises rounded, substantially spherical, biocompatible, substantially non-resorbable, finely divided ceramic particles.

35. The composition according to claim 34, wherein the ceramic particles are selected from the group consisting of calcium phosphate particles, calcium silicate particles, calcium carbonate particles and alumina particles.

36. The composition according to claim 35, wherein the ceramic particles are calcium phosphate particles.

37. The composition according to claim 36, wherein the calcium phosphate particles are selected from the group consisting of calcium hydroxyapatite particles, tetracalcium phosphate particles, calcium pyrophosphate particles, tricalcium phosphate particles, octacalcium phosphate particles, calcium fluorapatite particles, calcium carbonate apatite particles and mixtures thereof.

38. The composition according to claim 37, wherein the calcium phosphate particles are calcium hydroxyapatite particles.

39. The composition according to claim 21, wherein the desired tissue site is an osseous site.

40. The composition according to claim 21, wherein the desired tissue site is an osseous site in a state of osteoporosis.

41. In a biocompatible composition for augmenting tissue, the biocompatible composition comprising a biomaterial for augmenting a desired tissue site and a biocompatible, resorbable, lubricous carrier for the biomaterial, the improvement comprising a polysaccharide gel carrier, having a viscosity between about 20,000 centipoise to about 350,000 centipoise, the carrier maintaining the biomaterial homogeneously suspended in the biocompatible composition prior to augmentation of a desired tissue site and during introduction of the biocompatible composition to the desired site.

42. A substantially dehydrated biocompatible composition, comprising a biocompatible, resorbable, medium for suspending a biomaterial, the suspending medium comprising a dehydrated polysaccharide gel for maintaining the biomaterial suspended in the implant composition, the dehydrated composition being directly implantable into a living body.

43. The composition according to claim 42, wherein the composition is shaped into a preform for implantation into a desired tissue site.

44. The composition according to claim 42, wherein the polysaccharide gel comprises a polysaccharide selected from the group consisting of a cellulose polysaccharide, starch, chitin, chitosan, hyaluronic acid, hydrophobe modified polysaccharide, an alginate, a carrageenan, agar, agarose, an intramolecular complex of a polysaccharide, an oligosaccharide and a macrocyclic polysaccharide.

45. The composition according to claim 44, wherein the polysaccharide gel comprises a cellulose polysaccharide.

46. The composition according to claim 45, wherein the cellulose polysaccharide is selected from the group consisting of sodium carboxymethylcellulose, agar methylcellulose, hydroxypropyl methylcellulose, ethylcellulose, microcrystalline cellulose and oxidized cellulose.

47. The composition according to claim 46, wherein the cellulose polysaccharide is sodium carboxymethycellulose.

48. The composition according to claim 42, wherein the biomaterial is selected from the group consisting of a ceramic, a plastic and a metal.

49. The composition according to claim 48, wherein the biomaterial is a ceramic.

50. The composition according to claim 49, wherein the ceramic comprises rounded, substantially spherical, biocompatible, substantially non-resorbable, finely divided ceramic particles.

51. The composition according to claim 50, wherein the ceramic particles are selected from the group consisting of calcium phosphate particles, calcium silicate particles, calcium carbonate particles and alumina particles.

52. The composition according to claim 51, wherein the ceramic particles are calcium phosphate particles.

53. The composition according to claim 52, wherein the calcium phosphate particles are selected from the group consisting of calcium hydroxyapatite particles, tetracalcium phosphate particles, calcium pyrophosphate particles, tricalcium phosphate particles, octacalcium phosphate particles, calcium fluorapatite particles, calcium carbonate apatite particles and mixtures thereof.

54. The composition according to claim 53, wherein the calcium phosphate particles are calcium hydroxyapatite particles.

55. A method of making a substantially dehydrated biocompatible composition for implantation into a desired tissue site, comprising the step of drying a biocompatible composition comprising a biomaterial for augmenting a desired tissue site and a biocompatible, resorable, lubricious carrier for the biomaterial, the carrier comprising a polysaccharide gel having a viscosity of from about 20,000 to about 350,000.

56. A method of preparing and implanting a substantially dehydrated biocompatible composition, comprising the steps of drying a biocompatible composition comprising a biomaterial for augmenting a desired tissue site and a biocompatible, resorbable, lubricious carrier for the biomaterial, the carrier comprising a polysaccharide gel having a viscosity of from about 20,000 to about 350,000 centipoise, and implanting the dehydrated composition into a desired tissue site.

57. The carrier according to claim 1, further comprising an additive.

58. The carrier according to claim 57, wherein the additive is selected from the group consisting of a pH buffer, a stabilizer, and a surfactant.

59. The carrier according to claim 1, wherein the polysaccharide gel has a viscosity of from about 150,000 centipoise to about 250,000 centipoise.

60. The carrier according to claim 59, wherein the polysaccharide gel has a viscosity of from about 200,000 centipoise to about 250,000 centipoise.

61. The composition according to claim 21, further comprising an additive.

62. The composition according to claim 61, wherein the additive is selected from the group consisting of a pH buffer, a stabilizer, and a surfactant.

63. The composition according to claim 21, wherein the polysaccharide gel has a viscosity of from about 150,000 centipoise to about 250,000 centipoise.

64. The composition according to claim 63, wherein the polysaccharide gel has a viscosity of from about 200,000 centipoise to about 250,000 centipoise.

65. The composition according to claim 42, further comprising an additive.

66. The composition according to claim 65, wherein the additive is selected from the group consisting of a pH buffer, a stabilizer, and a surfactant.

67. A substantially dehydrated biocompatible composition, comprising a biocompatible, resorbable, medium for suspending a biomaterial, the suspending medium comprising a dehydrated polysaccharide gel for maintaining the biomaterial suspended in the implant composition,
wherein the polysaccharide gel has a viscosity before dehydration of from about 150,000 centipoise to about 250,000 centipoise.

68. A substantially dehydrated biocompatible composition, comprising a biocompatible, resorbable, medium for suspending a biomaterial, the suspending medium comprising a dehydrated polysaccharide gel for maintaining the biomaterial suspended in the implant composition,
wherein the polysaccharide gel has a viscosity before dehydration of from about 200,000 centipose to about 250,000 centipoise.

69. The method according to claim 55, wherein the biocompatible composition comprises an additive.

70. The method according to claim 69, wherein the additive is selected from the group consisting of a pH buffer, a stabilizer, and a surfactant.

71. The composition of claim 42, wherein the dehydrated composition is directly implantable into a body without a grinding or responding operation.

72. A substantially dehydrated biocompatible composition, comprising:
a biomaterial; and
means for suspending the biomaterial, the suspending means being in dehydrated form and being directly implantable into a body.

73. The composition of claim 72, wherein the suspending means comprises a dehydrated polysaccharide gel for maintaining the biomaterial suspended in the implant composition and being implantable into a body without a grinding or resuspending operation.

* * * * *

UNITED STATES PATENT AND TRADEMARK OFFICE
CERTIFICATE OF CORRECTION

PATENT NO.         : 7,060,287 B1
APPLICATION NO. : 09/626326
DATED                 : June 13, 2006
INVENTOR(S)       : William G. Hubbard and Timothy R. Devine It is certified that error appears in the above-identified patent and that said Letters Patent is hereby corrected as shown below:

In the claims, column 22, line 43 through column 26, line 62 delete claims 1-73 and insert:

--1.   A tissue augmentation material, comprising a polysaccharide gel having a viscosity between greater than about 200,000 to about 250,000 centipoise and a biomaterial, wherein the polysaccharide gel maintains the biomaterial homogeneously suspended in the tissue augmentation material prior to augmentation of a desired tissue site and during introduction of the tissue augmentation material to the desired site.

2.   The tissue augmentation material according to claim 1, wherein the polysaccharide gel is an aqueous polysaccharide gel.

3.   The tissue augmentation material according to claim 1, wherein the polysaccharide gel comprises a polysaccharide selected from the group consisting of a cellulose polysaccharide, starch, chitin, chitosan, hyaluronic acid, hydrophobe modified polysaccharide, an alginate, a carrageenan, agar, agarose, an intramolecular complex of a polysaccharide, an oligosaccharide and a macrocyclic polysaccharide.

4.   A tissue augmentation material, comprising a polysaccharide gel having a viscosity between greater than about 200,000 to about 250,000 centipoise and a biomaterial, wherein the polysaccharide gel maintains the biomaterial homogeneously suspended in the tissue augmentation material prior to augmentation of a desired tissue site and during introduction of the tissue augmentation material to the desired site, wherein the polysaccharide gel comprises a cellulose polysaccharide.

5.   The tissue augmentation material according to claim 4, wherein the cellulose polysaccharide is selected from the group consisting of sodium carboxymethlcellulose, agar methylcellulose, hydroxypropyl methylcellulose, ethylcellulose, microcrystalline cellulose and oxidized cellulose.

6.   The tissue augmentation material according to claim 5, wherein the cellulose polysaccharide is sodium carboxymethycellulose.

7.   The tissue augmentation material according to claim 1, wherein the polysaccharide gel comprises a solvent selected from the group consisting of water and aqueous alcohol.

UNITED STATES PATENT AND TRADEMARK OFFICE
CERTIFICATE OF CORRECTION

| | |
|---|---|
| PATENT NO. | : 7,060,287 B1 |
| APPLICATION NO. | : 09/626326 |
| DATED | : June 13, 2006 |
| INVENTOR(S) | : William G. Hubbard and Timothy R. Devine |

It is certified that error appears in the above-identified patent and that said Letters Patent is hereby corrected as shown below:

8. A tissue augmentation material, comprising a polysaccharide gel having a viscosity between greater than about 200,000 to about 250,000 centipoise and a biomaterial, wherein the polysaccharide gel maintains the biomaterial homogeneously suspended in the tissue augmentation material prior to augmentation of a desired tissue site and during introduction of the tissue augmentation material to the desired site , wherein the polysaccharide gel comprises a solvent selected from the group consisting of water and aqueous alcohol and further wherein the aqueous alcohol is selected from the group consisting of aqueous glycerol, aqueous isopropyl alcohol, aqueous ethanol, aqueous ethylene glycol and mixtures thereof.

9. A tissue augmentation material, comprising glycerin, a polysaccharide gel having a viscosity between greater than about 200,000 to about 250,000 centipoise and a biomaterial, wherein the polysaccharide gel maintains the biomaterial homogeneously suspended in the tissue augmentation material prior to augmentation of a desired tissue site and during introduction of the tissue augmentation material to the desired site and further wherein the polysaccharide gel is an aqueous polysaccharide gel.

10. A tissue augmentation material, comprising a polysaccharide gel having a viscosity between greater than about 200,000 to about 250,000 centipoise and a biomaterial, wherein the polysaccharide gel maintains the biomaterial homogeneously suspended in the tissue augmentation material prior to augmentation of a desired tissue site and during introduction of the tissue augmentation material to the desired site, wherein water and the glycerin are present in the aqueous polysaccharide gel in a ratio of from about 20 to 90:80 to 10.

11. A tissue augmentation material, comprising a polysaccharide gel having a viscosity between greater than about 200,000 to about 250,000 centipoise and a biomaterial, wherein the polysaccharide gel maintains the biomaterial homogeneously suspended in the tissue augmentation material prior to augmentation of a desired tissue site and during introduction of the tissue augmentation material to the desired site, wherein the water and the glycerin are present in the gel in a ratio of about 85:15.

12. The tissue augmentation material according to claim 10, wherein the biomaterial is selected from the group consisting of a ceramic, a plastic and a metal.

13. The tissue augmentation material according to claim 12, wherein the biomaterial is a ceramic.

UNITED STATES PATENT AND TRADEMARK OFFICE
CERTIFICATE OF CORRECTION

PATENT NO. : 7,060,287 B1
APPLICATION NO. : 09/626326
DATED : June 13, 2006
INVENTOR(S) : William G. Hubbard and Timothy R. Devine It is certified that error appears in the above-identified patent and that said Letters Patent is hereby corrected as shown below:

14. The tissue augmentation material according to claim 13, wherein the ceramic comprises rounded, substantially spherical, biocompatible, substantially nonresorbable, finely divided ceramic particles.

15. The tissue augmentation material according to claim 14, wherein the ceramic particles are selected from the group consisting of calcium phosphate particles, calcium silicate particles, calcium carbonate particles and alumina particles.

16. A biocompatible, resorbable, lubricous carrier for suspending a biomaterial in a tissue augmentation material, comprising a polysaccharide gel having a viscosity between greater than about 200,000 to about 250,000 centipoise and a biomaterial, wherein the polysaccharide gel maintains the biomaterial homogeneously suspended in the tissue augmentation material prior to augmentation of a desired tissue site and during introduction of the tissue augmentation material to the desired site, wherein the biomaterial comprises rounded, substantially spherical, biocompatible, substantially nonresorbable, finely divided ceramic particles, and wherein the ceramic particles are calcium phosphate particles.

17. The carrier according to claim 16, wherein the calcium phosphate particles are selected from the group consisting of calcium hydroxyapatite particles, tetracalcium phosphate particles, calcium pyrophosphate particles, tricalcium phosphate particles, octacalcium phosphate particles, calcium fluorapatite particles, calcium carbonate apatite particles and mixtures thereof.

18. The carrier according to claim 17, wherein the calcium phosphate particles are calcium hydroxyapatite particles.

19. The carrier according to claim 1, wherein the desired tissue site is an osseous site.

20. The carrier according to claim 19, wherein the desired tissue site is an osseous site in a state of osteoporosis.

21. A biocompatible composition for augmenting tissue, comprising a biomaterial for augmenting a desired tissue site and a biocompatible, resorbable, lubricous carrier for the biomaterial, the carrier comprising a polysaccharide gel having a viscosity between greater than about 200,000 to about 250,000 centipoise, wherein the carrier maintains the biomaterial homogeneously suspended in the biocompatible composition prior to augmentation of a desired tissue site and during introduction of the biocompatible composition to the desired site.

UNITED STATES PATENT AND TRADEMARK OFFICE
CERTIFICATE OF CORRECTION

| | |
|---|---|
| PATENT NO. | : 7,060,287 B1 |
| APPLICATION NO. | : 09/626326 |
| DATED | : June 13, 2006 |
| INVENTOR(S) | : William G. Hubbard and Timothy R. Devine |

It is certified that error appears in the above-identified patent and that said Letters Patent is hereby corrected as shown below:

22. The composition according to claim 21, wherein the polysaccharide gel is an aqueous polysaccharide gel.

23. The composition according to Claim 21, wherein the polysaccharide gel comprises a polysaccharide selected from the group consisting of a cellulose polysaccharide, starch, chitin, chitosan, hyaluronic acid, hydrophobe modified polysaccharide, an alginate, a carrageenan, agar, agarose, an intramolecular complex of a polysaccharide, an oligosaccharide and a macrocyclic polysaccharide.

24. A biocompatible composition for augmenting tissue, comprising a biomaterial for augmenting a desired tissue site and a biocompatible, resorbable, lubricous carrier for the biomaterial, the carrier comprising a polysaccharide gel having a viscosity between greater than about 200,000 to about 250,000 centipoise, wherein the carrier maintains the biomaterial homogeneously suspended in the biocompatible composition prior to augmentation of a desired tissue site and during introduction of the biocompatible composition to the desired site wherein the polysaccharide gel comprises a cellulose polysaccharide.

25. The composition according to claim 24, wherein the cellulose polysaccharide is selected from the group consisting of sodium carboxymethylcellulose, agar methylcellulose, hydroxypropyl methylcellulose, ethylcellulose, microcrystalline cellulose and oxidized cellulose.

26. The composition according to claim 25, wherein the cellulose polysaccharide is sodium carboxymethycellulose.

27. The composition according to claim 21, wherein the polysaccharide gel comprises a solvent selected from the group consisting of water and aqueous alcohol.

28. The composition according to claim 24, wherein the polysaccharide gel comprises a solvent selected from the group consisting of water and aqueous alcohol and further wherein the aqueous alcohol is selected from the group consisting of aqueous glycerol, aqueous isopropyl alcohol, aqueous ethanol, aqueous ethylene glycol and mixtures thereof.

UNITED STATES PATENT AND TRADEMARK OFFICE
CERTIFICATE OF CORRECTION

| | | |
|---|---|---|
| PATENT NO. | : 7,060,287 B1 | |
| APPLICATION NO. | : 09/626326 | |
| DATED | : June 13, 2006 | |
| INVENTOR(S) | : William G. Hubbard and Timothy R. Devine | |

It is certified that error appears in the above-identified patent and that said Letters Patent is hereby corrected as shown below:

29. A biocompatible composition for augmenting tissue, comprising glycerin, a biomaterial for augmenting a desired tissue site, and a biocompatible, resorbable, lubricous carrier for the biomaterial, the carrier comprising a polysaccharide gel having a viscosity between greater than about 200,000 to about 250,000 centipoise, wherein the carrier maintains the biomaterial homogeneously suspended in the biocompatible composition prior to augmentation of a desired tissue site and during introduction of the biocompatible composition to the desired site.

30. A biocompatible composition for augmenting tissue, comprising a biomaterial for augmenting a desired tissue site and a biocompatible, resorbable, lubricous carrier for the biomaterial, the carrier comprising a polysaccharide gel having a viscosity between greater than about 200,000 to about 250,000 centipoise, wherein the carrier maintains the biomaterial homogeneously suspended in the biocompatible composition prior to augmentation of a desired tissue site and during introduction of the biocompatible composition to the desired site, wherein water and the glycerin are present in the aqueous polysaccharide gel in a ratio of from about 20 to 90:80 to 10.

31. The composition according to claim 30, wherein the water and glycerin are present in the aqueous polysaccharide gel in a ratio of about 85:15.

32. The composition according to claim 21, wherein the biomaterial is selected from the group consisting of a ceramic, a plastic and a metal.

33. The composition according to claim 32, wherein the biomaterial is a ceramic.

34. The composition according to claim 33, wherein the ceramic comprises smooth, rounded, substantially spherical, biocompatible, substantially nonresorbable, finely divided ceramic particles.

35. The composition according to claim 34, wherein the ceramic particles are selected from the group consisting of calcium phosphate particles, calcium silicate particles, calcium carbonate particles and alumina particles.

UNITED STATES PATENT AND TRADEMARK OFFICE
CERTIFICATE OF CORRECTION

| | | |
|---|---|---|
| PATENT NO. | : 7,060,287 B1 | |
| APPLICATION NO. | : 09/626326 | |
| DATED | : June 13, 2006 | |
| INVENTOR(S) | : William G. Hubbard and Timothy R. Devine | |

It is certified that error appears in the above-identified patent and that said Letters Patent is hereby corrected as shown below:

36. A biocompatible composition for augmenting tissue, comprising a biomaterial for augmenting a desired tissue site and a biocompatible, resorbable, lubricous carrier for the biomaterial, the carrier comprising a polysaccharide gel having a viscosity between greater than about 200,000 to about 250,000 centipoise, wherein the carrier maintains the biomaterial homogeneously suspended in the biocompatible composition prior to augmentation of a desired tissue site and during introduction of the biocompatible composition to the desired site, wherein the biomaterial comprises rounded, substantially spherical, biocompatible, substantially nonresorbable, finely divided ceramic particles, and wherein the ceramic particles are calcium phosphate particles.

37. The composition according to claim 36, wherein the calcium phosphate particles are selected from the group consisting of calcium hydroxyapatite particles, tetracalcium phosphate particles, calcium pyrophosphate particles, tricalcium phosphate particles, octacalcium phosphate particles, calcium fluorapatite particles, calcium carbonate apatite particles and mixtures thereof.

38. The composition according to claim 37, wherein the calcium phosphate particles are calcium hydroxyapatite particles.

39. The composition according to claim 21, wherein the desired tissue site is an osseous site.

40. The composition according to claim 21, wherein the desired tissue site is an osseous site in a state of osteoporosis.

41. In a biocompatible composition for augmenting tissue, the biocompatible composition comprising a biomaterial for augmenting a desired tissue site and a biocompatible, resorbable, lubricous carrier for the biomaterial, the improvement comprising a polysaccharide gel carrier, having a viscosity between greater than about 200,000 to about 250,000 centipoise, the carrier maintaining the biomaterial homogeneously suspended in the biocompatible composition prior to augmentation of a desired tissue site and during introduction of the biocompatible composition to the desired site.

42. The tissue augmentation material according to claim 1, further comprising an additive.

43. The tissue augmentation material according to claim 42, wherein the additive is selected from the group consisting of a pH buffer, a stabilizer, and a surfactant.

UNITED STATES PATENT AND TRADEMARK OFFICE
CERTIFICATE OF CORRECTION

PATENT NO. : 7,060,287 B1
APPLICATION NO. : 09/626326
DATED : June 13, 2006
INVENTOR(S) : William G. Hubbard and Timothy R. Devine It is certified that error appears in the above-identified patent and that said Letters Patent is hereby corrected as shown below:

44. The composition according to claim 21, further comprising an additive.

45. The composition according to claim 44, wherein the additive is selected from the group consisting of a pH buffer, a stabilizer, and a surfactant.--

Signed and Sealed this

Sixteenth Day of January, 2007

JON W. DUDAS
*Director of the United States Patent and Trademark Office*